(12) United States Patent
Traverso et al.

(10) Patent No.: US 11,541,216 B2
(45) Date of Patent: Jan. 3, 2023

(54) METHODS FOR MANUFACTURING TISSUE INTERFACING COMPONENTS

(71) Applicants: Massachusetts Institute of Technology, Cambridge, MA (US); The Brigham and Women's Hospital, Inc., Boston, MA (US); Novo Nordisk A/S, Bagsvaerd (DK)

(72) Inventors: Carlo Giovanni Traverso, Newton, MA (US); Morten Revsgaard Frederiksen, Bagsvaerd (DK); Jorrit Jeroen Water, Frederiksberg (DK)

(73) Assignees: Massachusetts Institute of Technology, Cambridge, MA (US); Novo Nordisk A/S, Bagsvaerd (DK); The Brigham and Women's Hospital, Inc., Boston, MA (US)

( * ) Notice: Subject to any disclaimer, the term of this patent is extended or adjusted under 35 U.S.C. 154(b) by 21 days.

(21) Appl. No.: 16/691,514

(22) Filed: Nov. 21, 2019

(65) Prior Publication Data

US 2021/0154457 A1 May 27, 2021

(51) Int. Cl.
  *A61M 37/00* (2006.01)
  *A61K 9/16* (2006.01)
  *A61M 31/00* (2006.01)

(52) U.S. Cl.
  CPC ........... *A61M 37/0069* (2013.01); *A61K 9/16* (2013.01); *A61M 31/002* (2013.01);
  (Continued)

(58) Field of Classification Search
  None
  See application file for complete search history.

(56) References Cited

U.S. PATENT DOCUMENTS 2,601,767 A 7/1952 Wall
3,386,409 A 6/1968 Dawson
(Continued)

FOREIGN PATENT DOCUMENTS

CN 1820798 A 8/2006
CN 1887373 A 1/2007
(Continued)

OTHER PUBLICATIONS

International Search Report and Written Opinion for International Application No. PCT/EP2020/082967 dated Feb. 24, 2021 (15 pages).
(Continued)

*Primary Examiner* — Dominic Lazaro
(74) *Attorney, Agent, or Firm* — Finnegan, Henderson, Farabow, Garrett & Dunner, LLP

(57) ABSTRACT

Methods of manufacturing tissue interfacing components, such as solid needles comprising one or more therapeutic agents, are disclosed. In some embodiments, a method for manufacturing a tissue interfacing component comprises compressing a granular therapeutic agent within a mold cavity of a mold to form a solid tissue interfacing component. The mold cavity may define an elongated shape extending along a longitudinal axis from an opening of the mold cavity to a distal end of the mold cavity, and the granular therapeutic agent may be compressed by moving a mold punch along the longitudinal axis towards the distal end. After compressing the granular therapeutic agent to form the solid tissue interfacing component, the tissue interfacing component may be removed from the mold and subsequently inserted into tissue to deliver the therapeutic agent to a subject.

24 Claims, 7 Drawing Sheets

(52) U.S. Cl.
CPC .. *A61M 2202/0007* (2013.01); *A61M 2202/06* (2013.01); *A61M 2207/10* (2013.01)

(56) References Cited

U.S. PATENT DOCUMENTS

| | | | |
|---|---|---|---|
| 3,442,045 A | 5/1969 | Green | |
| 3,797,492 A | 3/1974 | Place | |
| 3,826,220 A | 7/1974 | Jacobson | |
| 4,236,525 A | 12/1980 | Sluetz et al. | |
| 4,239,040 A | 12/1980 | Hosoya et al. | |
| 4,407,283 A | 10/1983 | Reynolds | |
| 4,425,117 A | 1/1984 | Hugemann et al. | |
| 5,017,187 A | 5/1991 | Sullivan | |
| 5,217,449 A | 6/1993 | Yuda et al. | |
| 5,279,607 A | 1/1994 | Schentag et al. | |
| 5,318,557 A | 6/1994 | Gross | |
| 5,443,843 A | 8/1995 | Curatolo et al. | |
| 5,474,785 A | 12/1995 | Wright et al. | |
| 5,690,691 A | 11/1997 | Chen et al. | |
| 6,030,641 A | 2/2000 | Yamashita et al. | |
| 6,041,258 A | 3/2000 | Cigaina et al. | |
| 6,099,504 A | 8/2000 | Gross et al. | |
| 6,120,803 A | 9/2000 | Wong et al. | |
| 6,334,856 B1 | 1/2002 | Allen et al. | |
| 6,346,519 B1 | 2/2002 | Petrus | |
| 6,449,511 B1 | 9/2002 | Mintchev et al. | |
| 6,472,423 B1 | 10/2002 | Ross et al. | |
| 6,488,962 B1 | 12/2002 | Berner et al. | |
| 6,503,231 B1 | 1/2003 | Prausnitz et al. | |
| 6,615,084 B1 | 9/2003 | Cigaina | |
| 6,660,197 B1 * | 12/2003 | Buch-Rasmussen | A61J 3/06 264/109 |
| 6,684,104 B2 | 1/2004 | Gordon et al. | |
| 6,945,952 B2 | 9/2005 | Kwon | |
| 7,076,305 B2 | 7/2006 | Imran et al. | |
| 7,076,307 B2 | 7/2006 | Boveja | |
| 7,177,693 B2 | 2/2007 | Starkebaum | |
| 7,211,062 B2 | 5/2007 | Kwon | |
| 7,569,032 B2 | 8/2009 | Naimark et al. | |
| 7,620,454 B2 | 11/2009 | Dinsmoor et al. | |
| 7,666,844 B2 | 2/2010 | Buch-Rasmussen et al. | |
| 7,678,135 B2 | 3/2010 | Maahs et al. | |
| 7,704,264 B2 | 4/2010 | Ewers et al. | |
| 7,727,223 B2 * | 6/2010 | Potter | A61M 5/30 604/506 |
| 7,742,818 B2 | 6/2010 | Dinsmoor et al. | |
| 8,084,053 B2 | 12/2011 | Buch-Rasmussen et al. | |
| 8,241,308 B2 | 8/2012 | Kortenbach et al. | |
| 8,252,329 B2 | 8/2012 | Tzannis et al. | |
| 8,454,997 B2 | 6/2013 | Hansen et al. | |
| 8,518,308 B2 | 8/2013 | Khoshnevis | |
| 8,518,430 B2 | 8/2013 | Buch-Rasmussen et al. | |
| 8,562,589 B2 | 10/2013 | Imran | |
| 8,682,440 B2 | 3/2014 | Imran et al. | |
| 8,721,620 B2 | 5/2014 | Imran | |
| 8,734,429 B2 | 5/2014 | Imran et al. | |
| 8,759,284 B2 | 6/2014 | Imran | |
| 8,764,733 B2 | 7/2014 | Imran | |
| 8,781,591 B2 | 7/2014 | Imran et al. | |
| 8,809,269 B2 | 8/2014 | Imran | |
| 8,809,271 B2 | 8/2014 | Imran | |
| 8,846,040 B2 | 9/2014 | Imran | |
| 8,852,083 B2 | 10/2014 | Mintchev et al. | |
| 8,852,151 B2 | 10/2014 | Imran | |
| 8,958,879 B2 | 2/2015 | Imran et al. | |
| 8,969,293 B2 | 3/2015 | Imran | |
| 8,980,822 B2 | 3/2015 | Imran | |
| 9,149,617 B2 | 10/2015 | Imran | |
| 9,186,233 B2 | 11/2015 | Gobel et al. | |
| 9,205,127 B2 | 12/2015 | Imran | |
| 9,259,386 B2 | 2/2016 | Imran | |
| 9,283,179 B2 | 3/2016 | Imran | |
| 9,284,367 B2 | 3/2016 | Imran | |
| 9,314,228 B2 | 4/2016 | Miller | |
| 9,402,806 B2 | 8/2016 | Imran | |
| 9,402,807 B2 | 8/2016 | Imran | |
| 9,403,002 B2 | 8/2016 | Imran et al. | |
| 9,415,004 B2 | 8/2016 | Imran | |
| 9,456,988 B2 | 10/2016 | Imran | |
| 9,457,065 B2 | 10/2016 | Imran | |
| 9,486,414 B2 | 11/2016 | Imran | |
| 9,492,378 B2 | 11/2016 | Imran | |
| 9,511,121 B2 | 12/2016 | Imran | |
| 9,539,207 B2 | 1/2017 | Imran | |
| 9,629,799 B2 | 4/2017 | Imran | |
| 9,643,005 B2 | 5/2017 | Imran et al. | |
| 9,757,514 B2 | 9/2017 | Imran et al. | |
| 9,757,548 B2 | 9/2017 | Imran | |
| 9,808,510 B2 | 11/2017 | Imran | |
| 9,814,763 B2 | 11/2017 | Imran | |
| 9,844,505 B2 | 12/2017 | Imran | |
| 9,844,655 B2 | 12/2017 | Imran | |
| 9,861,683 B2 | 1/2018 | Imran | |
| 9,907,747 B2 | 3/2018 | Imran | |
| 10,300,259 B2 | 5/2019 | Ziaie et al. | |
| 10,632,251 B2 | 4/2020 | Imran et al. | |
| 10,667,936 B2 | 6/2020 | Gobel | |
| 2002/0055734 A1 | 5/2002 | Houzego et al. | |
| 2002/0082543 A1 | 6/2002 | Park et al. | |
| 2002/0138049 A1 | 9/2002 | Allen et al. | |
| 2002/0198470 A1 | 12/2002 | Imran et al. | |
| 2003/0060734 A1 | 3/2003 | Yokoi et al. | |
| 2003/0161881 A1 | 8/2003 | Hansen et al. | |
| 2003/0181788 A1 | 9/2003 | Yokoi et al. | |
| 2004/0025330 A1 | 2/2004 | Sylvia et al. | |
| 2004/0044308 A1 | 3/2004 | Naimark et al. | |
| 2004/0044364 A1 | 3/2004 | DeVries et al. | |
| 2004/0087893 A1 | 5/2004 | Kwon | |
| 2004/0111011 A1 | 6/2004 | Uchiyama et al. | |
| 2004/0122315 A1 | 6/2004 | Krill | |
| 2004/0193229 A1 | 9/2004 | Starkebaum et al. | |
| 2004/0215171 A1 | 10/2004 | Houzego et al. | |
| 2004/0253304 A1 | 12/2004 | Gross et al. | |
| 2005/0055014 A1 | 3/2005 | Coppeta et al. | |
| 2005/0055039 A1 | 3/2005 | Burnett et al. | |
| 2005/0065463 A1 | 3/2005 | Tobinaga et al. | |
| 2005/0065571 A1 | 3/2005 | Imran | |
| 2005/0075654 A1 | 4/2005 | Kelleher | |
| 2005/0124875 A1 | 6/2005 | Kawano et al. | |
| 2005/0131345 A1 | 6/2005 | Miller | |
| 2005/0147559 A1 | 7/2005 | von Alten | |
| 2005/0148847 A1 | 7/2005 | Uchiyama et al. | |
| 2005/0149142 A1 | 7/2005 | Starkebaum | |
| 2005/0171398 A1 | 8/2005 | Khait et al. | |
| 2005/0183733 A1 | 8/2005 | Kawano et al. | |
| 2005/0240239 A1 | 10/2005 | Boveja et al. | |
| 2005/0245986 A1 | 11/2005 | Starkebaum | |
| 2005/0250988 A1 | 11/2005 | Ewers et al. | |
| 2005/0267414 A1 | 12/2005 | Abraham-Fuchs et al. | |
| 2006/0004255 A1 | 1/2006 | Iddan et al. | |
| 2006/0030752 A1 | 2/2006 | Orihara | |
| 2006/0047309 A1 | 3/2006 | Cichocki | |
| 2006/0058829 A1 | 3/2006 | Sampson et al. | |
| 2006/0167339 A1 | 7/2006 | Gilad et al. | |
| 2006/0259074 A1 | 11/2006 | Kelleher et al. | |
| 2006/0271073 A1 | 11/2006 | Lam | |
| 2007/0021760 A1 | 1/2007 | Kelleher | |
| 2007/0033682 A1 | 2/2007 | Sretavan et al. | |
| 2007/0038181 A1 | 2/2007 | Melamud et al. | |
| 2007/0106175 A1 | 5/2007 | Uchiyama et al. | |
| 2007/0123809 A1 | 5/2007 | Weiss et al. | |
| 2007/0135825 A1 | 6/2007 | Binmoeller | |
| 2007/0156211 A1 | 7/2007 | Ferren et al. | |
| 2007/0156248 A1 | 7/2007 | Marco et al. | |
| 2007/0213659 A1 | 9/2007 | Trovato et al. | |
| 2008/0065168 A1 | 3/2008 | Bitton et al. | |
| 2008/0121825 A1 | 5/2008 | Trovato | |
| 2008/0188837 A1 | 8/2008 | Belsky et al. | |
| 2008/0214894 A1 | 9/2008 | Wedel | |
| 2008/0255543 A1 | 10/2008 | Tanaka et al. | |
| 2008/0262478 A1 | 10/2008 | Krijnsen et al. | |
| 2008/0269664 A1 | 10/2008 | Trovato et al. | |
| 2008/0294101 A1 | 11/2008 | Kawano | |
| 2008/0294143 A1 | 11/2008 | Tanaka et al. | |

(56) References Cited

U.S. PATENT DOCUMENTS

| | | |
|---|---|---|
| 2009/0005639 A1 | 1/2009 | Kawano et al. |
| 2009/0030473 A1 | 1/2009 | Khawaled et al. |
| 2009/0043278 A1 | 2/2009 | Tanaka et al. |
| 2009/0104250 A1 | 4/2009 | Boyden et al. |
| 2009/0112191 A1 | 4/2009 | Boyden et al. |
| 2009/0137866 A1 | 5/2009 | Boyden et al. |
| 2009/0234331 A1 | 9/2009 | Langereis et al. |
| 2009/0253954 A1 | 10/2009 | Katayama |
| 2009/0253999 A1 | 10/2009 | Aoki et al. |
| 2009/0275923 A1 | 11/2009 | Shimizu et al. |
| 2009/0281557 A1 | 11/2009 | Sander et al. |
| 2009/0299144 A1 | 12/2009 | Shigemori et al. |
| 2009/0306473 A1 | 12/2009 | Tanaka et al. |
| 2009/0306632 A1 | 12/2009 | Trovato et al. |
| 2009/0306633 A1 | 12/2009 | Trovato et al. |
| 2010/0003318 A1 | 1/2010 | Rigassi-Dietrich |
| 2010/0021536 A1 | 1/2010 | Gross |
| 2010/0033324 A1 | 2/2010 | Shimizu et al. |
| 2010/0049120 A1 | 2/2010 | Dijksman et al. |
| 2010/0056874 A1 | 3/2010 | Dijksman et al. |
| 2010/0063486 A1 | 3/2010 | Dijksman et al. |
| 2010/0179381 A1 | 7/2010 | Kawano et al. |
| 2010/0204678 A1 | 8/2010 | Imran |
| 2010/0228313 A1 | 9/2010 | Starkebaum et al. |
| 2010/0247453 A1 | 9/2010 | Jones |
| 2010/0286628 A1 | 11/2010 | Gross |
| 2010/0286668 A1 | 11/2010 | Tanaka et al. |
| 2010/0305656 A1 | 12/2010 | Imran et al. |
| 2010/0331827 A1 | 12/2010 | Shimizu |
| 2011/0017612 A1 | 1/2011 | Dijksman et al. |
| 2011/0034766 A1 | 2/2011 | Tanaka |
| 2011/0071589 A1 | 3/2011 | Starkebaum et al. |
| 2011/0087195 A1 | 4/2011 | Uhland et al. |
| 2011/0098651 A1 | 4/2011 | Falo, Jr. et al. |
| 2011/0106063 A1 | 5/2011 | Dijksman et al. |
| 2011/0106064 A1 | 5/2011 | Zou et al. |
| 2011/0152792 A1 | 6/2011 | Takada |
| 2011/0159137 A1 | 6/2011 | Ando et al. |
| 2011/0160129 A1 | 6/2011 | Imran |
| 2011/0160699 A1 | 6/2011 | Imran |
| 2011/0207998 A1 | 8/2011 | Katayama |
| 2011/0208270 A1 | 8/2011 | Imran et al. |
| 2012/0010590 A1 | 1/2012 | Imran |
| 2012/0095290 A1 | 4/2012 | Kawano |
| 2012/0116358 A1 | 5/2012 | Dijksman et al. |
| 2012/0143171 A1 | 6/2012 | Shimizu et al. |
| 2012/0305573 A1 | 12/2012 | Shi et al. |
| 2013/0108695 A1 | 5/2013 | Grenier et al. |
| 2013/0164371 A1 | 6/2013 | Imran |
| 2013/0164372 A1 | 6/2013 | Imran |
| 2013/0164373 A1 | 6/2013 | Imran |
| 2013/0165372 A1 | 6/2013 | Imran |
| 2013/0165373 A1 | 6/2013 | Imran |
| 2013/0165772 A1 | 6/2013 | Traverso et al. |
| 2013/0165859 A1 | 6/2013 | Imran |
| 2013/0171244 A1 | 7/2013 | Imran |
| 2013/0171245 A1 | 7/2013 | Imran |
| 2013/0171246 A1 | 7/2013 | Imran |
| 2013/0171247 A1 | 7/2013 | Imran |
| 2013/0172257 A1 | 7/2013 | Imran |
| 2013/0172672 A1 | 7/2013 | Iddan et al. |
| 2013/0172694 A1 | 7/2013 | Zou et al. |
| 2013/0177527 A1 | 7/2013 | Imran |
| 2013/0177550 A1 | 7/2013 | Imran |
| 2013/0189353 A1 | 7/2013 | Imran |
| 2013/0195970 A1 | 8/2013 | Imran |
| 2013/0197440 A1 | 8/2013 | Zou et al. |
| 2013/0204233 A1 | 8/2013 | Zou et al. |
| 2013/0274659 A1 | 10/2013 | Imran et al. |
| 2013/0338583 A1 | 12/2013 | Imran |
| 2014/0135698 A1 | 5/2014 | Zou et al. |
| 2014/0163637 A1 | 6/2014 | Imran et al. |
| 2014/0221912 A1 | 8/2014 | Imran |
| 2014/0221927 A1 | 8/2014 | Imran et al. |
| 2014/0234418 A1 | 8/2014 | Coulter et al. |
| 2014/0243921 A1 | 8/2014 | Imran et al. |
| 2014/0256631 A1 | 9/2014 | Imran |
| 2014/0257238 A1 | 9/2014 | Imran |
| 2014/0276595 A1 | 9/2014 | Imran |
| 2014/0335168 A1 | 11/2014 | Imran |
| 2014/0336112 A1 | 11/2014 | Imran |
| 2014/0378764 A1 | 12/2014 | Mintchev et al. |
| 2015/0011874 A1 | 1/2015 | Amoako-Tuffour et al. |
| 2015/0023962 A1 | 1/2015 | Imran |
| 2015/0025496 A1 | 1/2015 | Imran |
| 2015/0051589 A1 | 2/2015 | Sako et al. |
| 2015/0064241 A1 | 3/2015 | Conrad |
| 2015/0141967 A1 | 5/2015 | Pardoel et al. |
| 2015/0147390 A1 | 5/2015 | Imran |
| 2015/0174076 A1 | 6/2015 | Harris et al. |
| 2015/0174400 A1 | 6/2015 | Imran et al. |
| 2015/0238571 A1 | 8/2015 | Imran |
| 2015/0328287 A1 | 11/2015 | Morales et al. |
| 2015/0329630 A1 | 11/2015 | Morales et al. |
| 2015/0329631 A1 | 11/2015 | Morales et al. |
| 2015/0329633 A1 | 11/2015 | Morales et al. |
| 2016/0015648 A1 | 1/2016 | Gross et al. |
| 2016/0022873 A1 | 1/2016 | Besner et al. |
| 2016/0144000 A1 | 5/2016 | Imran |
| 2016/0158516 A1 | 6/2016 | Imran |
| 2016/0166650 A1 | 6/2016 | Imran |
| 2016/0220759 A1 | 8/2016 | Enggaard et al. |
| 2016/0235663 A1 | 8/2016 | Zou et al. |
| 2017/0027520 A1 | 2/2017 | Terry et al. |
| 2017/0027862 A1 | 2/2017 | Imran |
| 2017/0028195 A1 | 2/2017 | Imran et al. |
| 2017/0043144 A1 | 2/2017 | Imran |
| 2017/0049708 A1 | 2/2017 | Imran |
| 2017/0050005 A1 | 2/2017 | Imran |
| 2017/0051051 A1 | 2/2017 | Imran et al. |
| 2017/0066824 A1 | 3/2017 | Imran et al. |
| 2017/0066841 A1 | 3/2017 | Imran et al. |
| 2017/0081399 A1 | 3/2017 | Imran |
| 2017/0087299 A1 | 3/2017 | Anderson |
| 2017/0100459 A1 | 4/2017 | Imran |
| 2017/0106099 A1 | 4/2017 | Bellinger et al. |
| 2017/0174758 A1 | 6/2017 | Imran |
| 2017/0189269 A1 | 7/2017 | Fischer et al. |
| 2017/0189659 A1 | 7/2017 | Imran |
| 2017/0216589 A1 | 8/2017 | Imran et al. |
| 2017/0231902 A1 | 8/2017 | Imran |
| 2017/0258732 A1 | 9/2017 | Imran et al. |
| 2017/0258833 A1 | 9/2017 | Imran et al. |
| 2017/0296092 A1 | 10/2017 | Jones et al. |
| 2018/0008771 A1 | 1/2018 | Imran et al. |
| 2018/0015146 A1 | 1/2018 | Imran |
| 2018/0037643 A9 | 2/2018 | Imran et al. |
| 2018/0049725 A1 | 2/2018 | Jones et al. |
| 2018/0064366 A1 | 3/2018 | Sweeney et al. |
| 2018/0168488 A1 | 6/2018 | Jones et al. |
| 2018/0193621 A1 | 7/2018 | Bonner et al. |
| 2018/0250503 A1 | 9/2018 | Enomoto et al. |
| 2018/0296814 A1 | 10/2018 | Shimizu |
| 2018/0311154 A1 | 11/2018 | Kanasty et al. |
| 2018/0311168 A1* | 11/2018 | Tian ............. A61P 19/02 |
| 2019/0046721 A1 | 2/2019 | Lordanov et al. |
| 2019/0133937 A1 | 5/2019 | Imran et al. |
| 2019/0223846 A1 | 7/2019 | Kerkhof et al. |
| 2019/0254966 A1 | 8/2019 | Bellinger et al. |
| 2019/0262265 A1 | 8/2019 | Bellinger et al. |
| 2019/0282791 A1 | 9/2019 | Jones et al. |
| 2019/0321613 A1 | 10/2019 | Jones et al. |
| 2020/0009371 A1 | 1/2020 | Langer et al. |
| 2020/0129441 A1 | 4/2020 | Abramson et al. |
| 2020/0147298 A1 | 5/2020 | Traverso et al. |
| 2020/0205729 A1 | 7/2020 | Jones et al. |
| 2020/0246545 A1 | 8/2020 | Langer et al. |
| 2020/0306515 A1 | 10/2020 | Traverso et al. |
| 2020/0324095 A1 | 10/2020 | Traverso et al. |

FOREIGN PATENT DOCUMENTS

| | | |
|---|---|---|
| CN | 100998904 A | 7/2007 |
| CN | 100376299 C | 3/2008 |

(56) References Cited

FOREIGN PATENT DOCUMENTS

| | | |
|---|---|---|
| CN | 106137099 A | 11/2016 |
| CN | 106730284 A | 5/2017 |
| DE | 102005032290 A1 | 1/2007 |
| DE | 102014015919 A1 | 12/2015 |
| EP | 0227060 A2 | 7/1987 |
| EP | 0415671 A2 | 3/1991 |
| EP | 1784140 A1 | 5/2007 |
| EP | 2201938 A1 | 6/2010 |
| FR | 2794654 A1 | 12/2000 |
| JP | 55166142 | 12/1980 |
| JP | 58019232 | 2/1983 |
| JP | 2003093332 A | 4/2003 |
| JP | 2003325438 A | 11/2003 |
| JP | 2004222998 A | 8/2004 |
| JP | 2013022291 A | 2/2013 |
| KR | 20180053852 A | 5/2018 |
| WO | 2000/062759 A1 | 10/2000 |
| WO | WO 2001/026602 A1 | 4/2001 |
| WO | 2001/058424 A1 | 8/2001 |
| WO | 2006/020929 A2 | 2/2006 |
| WO | 2006/084164 A2 | 8/2006 |
| WO | 2006/125074 A1 | 11/2006 |
| WO | 2006/131522 A1 | 12/2006 |
| WO | 2007/093806 A1 | 8/2007 |
| WO | 2007/127976 A2 | 11/2007 |
| WO | 2008/111078 A2 | 9/2008 |
| WO | 2009/063375 A1 | 5/2009 |
| WO | 2009/063376 A1 | 5/2009 |
| WO | 2009/063377 A1 | 5/2009 |
| WO | 2010/140401 A1 | 12/2010 |
| WO | 2011/141372 A1 | 11/2011 |
| WO | 2013/101908 A1 | 7/2013 |
| WO | 2014/007824 A1 | 1/2014 |
| WO | 2016/067087 A2 | 5/2016 |
| WO | 2016/102526 A1 | 6/2016 |
| WO | 2016/155671 A1 | 10/2016 |
| WO | WO 2016/179120 A1 | 11/2016 |
| WO | 2016/193375 A1 | 12/2016 |
| WO | 2017/004623 A1 | 1/2017 |
| WO | 2017/044665 A1 | 3/2017 |
| WO | 2018/112235 A1 | 6/2018 |
| WO | 2018/112245 A1 | 6/2018 |
| WO | 2018/182612 A1 | 10/2018 |
| WO | 2018/182623 A1 | 10/2018 |
| WO | 2018/182641 A1 | 10/2018 |
| WO | 2018/183932 A1 | 10/2018 |
| WO | 2018/183934 A1 | 10/2018 |
| WO | 2018/183941 A2 | 10/2018 |
| WO | 2018/213576 A1 | 11/2018 |
| WO | 2018/213579 A1 | 11/2018 |
| WO | 2018/213582 A1 | 11/2018 |
| WO | 2018/213588 A1 | 11/2018 |
| WO | 2018/213593 A1 | 11/2018 |
| WO | 2018/213600 A1 | 11/2018 |
| WO | 2019/036363 A1 | 2/2019 |
| WO | 2019/036382 A1 | 2/2019 |
| WO | 2019/121686 A1 | 6/2019 |
| WO | 2019/147824 A1 | 8/2019 |
| WO | 2020/157324 A1 | 8/2020 |
| WO | 2020/160399 A1 | 8/2020 |

OTHER PUBLICATIONS

Banerjee et al., "Intestinal micropatches for oral insulin delivery." J. Drug Target. Mar. 2017, vol. 25, No. 7, pp. 608-615.
Diabetes Control and Complications Trial Research Group. "The effect of intensive diabetes treatment on the development and progression of long-term complications in insulin-dependent diabetes mellitus." Sep. 1993, N. Engl. J. Med., vol. 329, No. 14, pp. 977-986.
Cision PR Newswire. "Non-Insulin Therapies for Diabetes: GLP-1 Agonists, DPP4 Inhibitors and SGLT2 Inhibitors, 2016-2026." Retrieved from www.prnewswire.com/news-releases/non-insulin-therapies-for-diabetes-glp-1-agonists-dpp4- inhibitors-and-sglt2-inhibitors-2016--2026-300317435.html. Aug. 23, 2016, 11 pages.
FDA Guidance for Industry, "Food-effect bioavailability and Fed Bioequialence Studies." Dec. 2002, U.S. Department of Health and Human Services, Food and Drug Administration, Center for Drug Evaluation and Research (CDER), 12 pages.
Abell et al., "Gastric Electrical Stimulation for Medically Refractory Gastroparesis." Aug. 2003, Gastroenterology, vol. 125, No. 2, pp. 421-428.
Abrahamsson et al., "A novel in vitro and numerical analysis of shear-induced drug release from extended-release tablets in the fed stomach." Aug. 2005, Pharm Res., vol. 22, No. 8, pp. 1215-1226.
Aguirre et al., "Current status of selected oral peptide technologies in advanced preclinical development and in clinical trials." Nov. 2016, Adv Drug Deliv Rev., vol. 106, Pt B, pp. 223-241 .Epub Feb. 24, 2016.
Ahmad et al., "Enhancement of oral insulin bioavailability: in vitro and in vivo assessment of nanoporous stimuli-responsive hydrogel microparticles." Mar. 2016, Expert Opin Drug Deliv., vol. 13, No. 5, pp. 621-632.
Alcock et al., "Long-term thermostabilization of live poxviral and adenoviral vaccine vectors at supraphysiological temperatures in carbohydrate glass." Sci Transl Med., Feb. 2010, vol. 2, No. 19, pp. 1-9.
Anderloni et al., "Advances, problems, and complications of polypectomy." Clin Exp Gastroenterol., Aug. 2014, vol. 30, No. 7, pp. 285-296.
Andrews et al., "Mucoadhesive polymeric platforms for controlled drug delivery." Eur J Pharm Biopharm, Mar. 2009, vol. 71, No. 3, pp. 505-518.
Aran et al., "An oral microjet vaccination system elicits antibody production in rabbits." Sci Transl Med, Mar. 2017, vol. 9, No. 380, pp. 1-10.
Bass et al., "Gastrointestinal safety of an extended-release, nondeformable, oral dosage form (OROS: a retrospective study." Drug Saf., Dec. 2002, vol. 25, No. 14, pp. 1021-1033.
Becker et al., "Novel orally swallowable IntelliCap(®) device to quantify regional drug absorption in human GI tract using diltiazem as model drug." AAPS PharmSciTech., Dec. 2014, vol. 15, No. 6, pp. 1490-1497.
Boddupalli et al., "Mucoadhesive drug delivery system: An overview." J Adv Pharm Technol Res., Oct. 2010, vol. 1, No. 4, pp. 381-387.
Bolondi et al., "Measurement of gastric emptying time by real-time ultrasonography." Gastroenterology, Oct. 1985, vol. 89, No. 4, pp. 752-759.
Brayden et al., "Oral delivery of peptides: opportunities and issues for translation." Adv Drug Deliv Rev., Nov. 2016, vol. 106, No. Pt B, pp. 193-195.
Brunton, "GLP-1 receptor agonists vs. DPP-4 inhibitors for type 2 diabetes: is one approach more successful or preferable than the other?" Int J Clin Pract., May 2014, vol. 68, No. 5, pp. 557-567.
Bui et al., "Prediction of viscosity of glucose and calcium chloride solutions." J. Food Eng., May 2004, vol. 62, No. 4, pp. 345-349.
Buse et al., "Liraglutide once a day versus exenatide twice a day for type 2 diabetes: a 26-week randomised, parallel-group, multinational, open-label trial (LEAD-6)." Lancet. Jul. 2009, vol. 374, No. 9683, pp. 39-47.
Caffarel-Salvador et al., "Oral delivery of biologies using drug-device combinations." Curr Opin Pharmacol., Oct. 2017, vol. 36, pp. 8-13.
Calvert et al., "Management of type 2 diabetes with multiple oral hypoglycaemic agents or insulin in primary care retrospective cohort study" Br. J. Gen. Pract., Jun. 2007, vol. 57, No. 539, 6 pages.
Camilleri et al., "Axial forces during gastric emptying in health and models of disease." Dig. Dis. Sci., Dec. 1994; vol. 39, No. 12, p. 14S-17S.
Carino et al., "Oral insulin delivery." Adv Drug Deliv Rev., Feb. 1999, vol. 35, No. 2-3, pp. 249-257.

(56) References Cited

OTHER PUBLICATIONS

Carlson, "Ousting the "ouch factor" in drug delivery." Biotechnol Healthc., Dec. 2007, vol. 4, No. 6, pp. 15-16.
Chaddock et al., "Novel MRI tests of orocecal transit time and whole gut transit time: studies in normal subjects." Neurogastroenterol Motil., Feb. 2014, vol. 26, No. 2, pp. 205-214.
Cui et al., "The study of a remote-controlled gastrointestinal drug delivery and sampling system." Telemed J E Health., Sep. 2008, vol. 14, No. 7, pp. 715-719.
Dallel et al.,"Gestion des seringues a insuline utilisées par les diabétiques insulino-traités a domicile. A propos de 100 patients [Disposal of insulin syringes by diabetic patients. Report of 100 patients]." Tunis Med., Jul. 2005, vol. 83, No. 7, pp. 390-392. French.
Degen et al., "Variability of gastrointestinal transit in healthy women and men." Gut., Aug. 1996, vol. 39, No. 2, pp. 299-305.
Delvaux et al., "Clinical evaluation of the use of the M2A patency capsule system before a capsule endoscopy procedure, in patients with known or suspected intestinal stenosis." Endoscopy., Sep. 2005, vol. 37, No. 9, pp. 801-807.
Defronzo et al., "Effects of exenatide versus sitagliptin on postprandial glucose, insulin and glucagon secretion, gastric emptying, and caloric intake: a randomized, cross-over study.", Curr Med Res Opin., Oct. 2008, vol. 24, No. 10, pp. 2943-2952.
Des Rieux et al., "Nanoparticles as potential oral delivery systems of proteins and vaccines: a mechanistic approach." J Control Release. Nov. 2006, vol. 116, No. 1, pp. 1-27.
Diamond et al., "Experience with a pill-swallowing enhancement aid." Clin Pediatr (Phila). Apr. 2010, vol. 49, No. 4, pp. 391-393.
Domokos et al., "Geometry and self-righting of turtles." Proc Biol Sci. Jan. 2008, vol. 275, No. 1630, pp. 11-17.
Eisen et al., "Complications of upper Gl endoscopy." Gastrointest Endosc. Jun. 2002, vol. 55, No. 7, pp. 784-793.
Eldor et al., "Glucose-reducing effect of the ORMD-0801 oral insulin preparation in patients with uncontrolled type 1 diabetes: a pilot study." PLoS One., Apr. 2013, vol. 8, No. 4, p. e59524.
Ensign et al., "Oral drug delivery with polymeric nanoparticles: the gastrointestinal mucus barriers." Adv Drug Deliv Rev., May 2012, vol. 64, No. 6, pp. 557-570.
Fallowfield et al., "Patients' preference for administration of endocrine treatments by injection or tablets: results from a study of women with breast cancer." Ann Oncol., Feb. 2006, vol. 17, No. 2, pp. 205-210.
Ferrua et al., "Modeling the fluid dynamics in a human stomach to gain insight of food digestion." J Food Sci., Sep. 2010, vol. 75, No. 7, pages R151-R162.
Finkelstone et al., "Etiology of small bowel thickening on computed tomography." Can J Gastroenterol, Dec. 2012, vol. 26, No. 12, pp. 897-901.
Foster et al., "Effect of Texture of Plastic and Elastic Model Foods on the Parameters of Mastication." J Neurophysiol, Jun. 2006, vol. 95, No. 6, pp. 3469-3479.
Fox et al., "Fabrication of Sealed Nanostraw Microdevices for Oral Drug Delivery." ACS Nano., Jun. 2016, vol. 10, No. 6 5873-81.
Fox et al., "Micro/nanofabricated Platforms for Oral Drug Delivery." J Control Release., Dec. 2015, vol. 219, No. 34, pp. 431-444.
Gao et al., "Biodegradable, pH-responsive carboxymethyl cellulose/poly(acrylic acid) hydrogels for oral insulin delivery." Macromol Biosci., Apr. 2014, vol. 14, No. 4, pp. 565-575.
Gilroy et al., "Controlled release of biologies for the treatment of type 2 diabetes." J Control Release, Oct. 2016, vol. 240, No. 14, pp. 151-164. Available online Dec. 2, 2015.
Giudice et al., "Needle-free vaccine delivery."Adv Drug Deliv Rev., Apr. 2006, vol. 58, No. 1, pp. 68-89. Available online Mar. 24, 2006.
Glendorf et al., "Importance of the Solvent-Exposed Residues of the Insulin B Chain alpha-Helix for Receptor Binding." Biochemistry. Apr. 2008, vol. 47, No. 16, pp. 4743-4751.
Gregory et al., "Pattern of gastric emptying the pig: relation to feeding." Br J Nutr. Jan. 1990, vol. 64, No. 1, pp. 45-58.

Guilloteau et al., "Nutritional programming of gastrointestinal tract development. Is the pig a good model for man?" Nutr Res Rev., Jun. 2010, vol. 23, No. 1, pp. 4-22.
Gupta et al., "A permeation enhancer for increasing transport of therapeutic macromolecules across the intestine." J Control Release, Dec. 2013, vol. 172, No. 2, pp. 541-549. Available online May 14, 2013.
Harding et al., "The crystal structure of insulin. II. An investigation of rhombohedral zinc insulin crystals and a report of other crystalline forms." J Mol Biol. Mar. 1966, vol. 16, No. 1, pp. 212-226.
Harrison, "Insulin in Alcoholic Solution By the Mouth." Br Med J. Dec. 1923, vol. 2, No. 3286, pp. 1204-1205.
Hay, "Can 'Robotic' Pills Replace Injections?" The Wall Street Journal. Feb. 17, 2014, 4 pages. Retrieved from www.wsj.com/articles/can-8216robotic8217-pills-replace-injections-1392681501?tesla=y.
He et al., "Scalable fabrication of size-controlled chitosan nanoparticles for oral delivery of insulin", Biomaterials, Jun. 2017, vol. 130, No. 7, pp. 28-41.
Hoebler et al., "Particle size of solid food after human mastication and in vitro simulation of oral breakdown." Int J Food Sci Nutr, Jan. 2000, vol. 51, No. 5, pp. 353-366.
Höög et al., "Capsule retentions and incomplete capsule endoscopy examinations: an analysis of 2300 examinations." Gastroenterol Res Pract., Sep. 2011, vol. 2012, Article ID 518718, pp. 1-7.
Hvid et al., "In situ phosphorylation of Akt and ERK1/2 in rat mammary gland, colon, and liver following treatment with human insulin and IGF-1." Toxicol Pathol., Jun. 2011, vol. 39, No. 4, pp. 623-640.
Ingersoll et al., "The impact of medication regimen factors on adherence to chronic treatment: a review of literature." J Behav Med., Jun. 2008, vol. 31, No. 3, pp. 213-224.
Jalabert-Malbos et al., "Particle size distribution in the food bolus after mastication of natural foods." Food Qual Prefer., Jul. 2007, vol. 18, No. 5 , pp. 803-812.
Kalantzi et al., "Characterization of the human upper gastrointestinal contents under conditions simulating bioavailability/bioequivalence studies." Pharm Res., Jan. 2006, vol. 23, No. 1, pp. 165-176.
Kim et al., "Droplet-born air blowing: Novel dissolving microneedle fabrication", J. Control. Release, Jun. 2013, vol. 170, No. 3, pp. 430-436.
Kong et al., "Disintegration of solid foods in human stomach." J Food Sci., Jun. 2008, vol. 73, No. 5, pp. R67-R80.
Lahiji et al., "A patchless dissolving microneedle delivery system enabling rapid and efficient transdermal drug delivery." Sci Rep., Jan. 2015, vol. 21, No. 5, p. 7914.
Lee et al., "Formulation of two-layer dissolving polymeric microneedle patches for insulin transdermal delivery in diabetic mice." J Biomed Mater Res. Part A., Jan. 2017, vol. 105, No. 1, pp. 84-93. Available online Aug. 29, 2016.
Ling et al., "Dissolving polymer microneedle patches for rapid and efficient transdermal delivery of insulin to diabetic rats." Acta Biomater., Nov. 2013, vol. 9, No. 11, pp. 8952-8961. Available online Jun. 29, 2013.
Marasini et al., "Oral delivery of nanoparticle-based vaccines." Expert Rev Vaccines, Nov. 2014, vol. 13, No. 11, pp. 1361-1376. Published online Aug. 26, 2014.
Mathiowitz et al., "Biologically erodable microspheres as potential oral drug delivery systems." Nature, Mar. 1997, vol. 386, No. 6623, pp. 410-414.
Metcalf et al., "Simplified assessment of segmental colonic transit." Gastroenterology, Jan. 1987, vol. 92, No. 1, pp. 40-47.
Mikiewicz et al., "Soluble insulin analogs combining rapid- and long-acting hypoglycemic properties—From an efficient *E. coli* expression system to a pharmaceutical formulation." PLoS One, Mar. 2017, vol. 12, No. 3, p. e0172600.
More, "Bluetooth low energy: wireless connectivity for medical monitoring." J Diabetes Sci Technol., Mar. 2010, vol. 4, No. 2, pp. 457-463.
Morishita et al., "Novel oral insulin delivery systems based on complexation polymer hydrogels: single and multiple administra-

(56) References Cited

OTHER PUBLICATIONS tion studies in type 1 and 2 diabetic rats." J Control Release, Feb. 2006, Volume, No 3, pp. 587-594. Available online Dec. 2, 2005.
Moroz et al., "Oral delivery of macromolecular drugs: Where we are after almost 100 years of attempts." Adv Drug Deliv Rev., Jun. 2016, vol. 101, pp. 108-121. Available online Jan. 27, 2016.
Nahata et al., "Extemporaneous drug formulations." Clin Ther., Nov. 2008, vol. 30, No. 11, pp. 2112-2119.
Nakamura et al., "Oral insulin delivery using P(MAA-g-EG) hydrogels: effects of network morphology on insulin delivery characteristics." J Control Release, Mar. 2004, vol. 95, No. 3, pp. 589-599.
Nordquist et al., "Novel microneedle patches for active insulin delivery are efficient in maintaining glycaemic control: an initial comparison with subcutaneous administration." Pharm Res., Jul. 2007, vol. 24, No. 7, pp. 1381-1388.
Omre, "Bluetooth low energy: wireless connectivity for medical monitoring." J Diabetes Sci Technol., Mar. 2010, vol. 4, No. 2, pp. 457-463.
Ortiz et al., "Metallic ions released from stainless steel, nickel-free, and titanium orthodontic alloys: toxicity and DNA damage." Am J Orthod Dentofacial Orthop., Sep. 2011, vol. 140, No. 3, pp. e115-22.
Ortiz et al., "Identification of insulin variants using Raman spectroscopy." Anal Biochem, Sep. 2004, vol. 332, No. 2, pp. 245-252. Available online Jul. 24, 2004.
Osterberg et al., "Adherence to medication." N Engl J Med., Aug. 2005, vol. 353, No. 5, pp. 487-497.
Outlander Anatomy, Anatomy Lesson #44: "Terrific Tunnel—GI System, Part 1". Oct. 18, 2016. 43 pages. Retrieved from www.outlanderanatomy.com/anatomy-lesson-44-terrific-tunnel-gi-system-part-1/.
Pawar et al., "Targeting of gastrointestinal tract for amended delivery of protein/peptide therapeutics: strategies and industrial perspectives." J Control Release, Dec. 2014, vol. 196, No. 28, pp. 168-183. Available online Oct. 14, 2014.
Podolsky, "Healing the epithelium: Solving the problem from two sides," J Gastroenterol., Jan. 1997, vol. 32, pp. 122-126.
Pratley et al., "Liraglutide versus sitagliptin for patients with type 2 diabetes who did not have adequate glycaemic control with metformin: a 26-week, randomised, parallel-group, open-label trial." Lancet, Apr. 2010, vol. 375, No. 9724, pp. 1447-1456.
Prego et al., "The potential of chitosan for the oral administration of peptides." Expert Opin Drug Deliv., Sep. 2005, vol. 2, No. 5, pp. 843-854.
Rapaccini et al., "Gastric wall thickness in normal and neoplastic subjects: a prospective study performed by abdominal ultrasound." Gastrointest Radiol., Jul. 1988, vol. 13, No. 3, pp. 197-199.
Ravi et al., "Needle free injection technology: A complete insight." Int J Pharm Investig., Oct. 2015, vol. 5, No. 4, pp. 192-199.
Römgens et al., "Monitoring the penetration process of single microneedles with varying tip diameters." J Mech Behav Biomed Mater., Dec. 2014, vol. 40, pp. 397-405. Available online Oct. 8, 2014.
Saniocki, "New insights into tablet sticking: characterization and quantification of sticking to punch surfaces during tablet manufacter by direct compaction. PhD Thesis." University Hamburg., 2014, 159 pages.
Santonen et al., "Review on toxicity of stainless steel." Finnish Institute of Occupational Health, Helsinki, Nov. 2010. 87 pages. Retrieved from: www.bssa.org.uk/cms/File/Review on Toxicity of Stainless Steel Finnish Health Tnstitute.pdf.
Schmidt et al., "Viscosity and electrolyte concentrations in gastric juice from cystic fibrosis children compared to healthy children." Eur J Pediatr., May 1981, vol. 136, No. 2, pp. 193-197.
Schoellhammer et al., "Of microneedles and ultrasound: Physical modes of gastrointestinal macromolecule delivery." Tissue Barriers, Feb. 2016, vol. 4, No. 2, e1150235, 5 pages.
Schoellhammer et al., "Ultrasound-Mediated Delivery of RNA to Colonic Mucosa of Live Mice." Gastroenterology, Apr. 2017, vol. 152, No. 5, pp. 1151-1160.

Schoellhammer et al., "Ultrasound-mediated gastrointestinal drug delivery." Sci Transl Med., Oct. 2015, vol. 7, No. 310, p. 1-11.
Schwartz et al., "Electrical stimulation of the isolated rat intestine in the presence of nutrient stimulus enhances glucagon-like peptide-1 release." Physiol Meas., Sep. 2010, vol. 31, No. 9, pp. 1147-1159.
Sharma et al., "Development of enteric submicron particle formulation of papain for oral delivery." Int J Nanomedicine, 2011, vol. 6, pp. 2097-2111.
Sher et al., "Simulation of peristaltic flow of chyme in small intestine for couple stress fluid." Meccanica, Feb. 2014, vol. 49, pp. 325-334. Published online Aug. 29, 2013.
Sokolowski et al., "Needle phobia: etiology, adverse consequences, and patient management." Dent Clin North Am., Oct. 2010, vol. 54, No. 4, pp. 731-744.
Stewart et al., "In vitro and ex vivo strategies for intracellular delivery." Nature, Oct. 2016, vol. 538, No. 7624, pp. 183-192.
Tang et al., "Biodegradable polymer nanoparticles that rapidly penetrate the human mucus barrier." Proc Natl Acad Sci U S A., Nov. 2009, vol. 106, No. 46, p. 19268-73.
Taverner et al., "Enhanced paracellular transport of insulin can be achieved via transient induction of myosin light chain phosphorylation." J Control Release, Jul. 2015, vol. 28, No. 210, pp. 189-197. Available online May 14, 2015.
Thomas, "Gut motility, sphincters and reflex control." Anaesth Intensive Care Med., Feb. 2006, vol. 7, No. 2, pp. 57-58.
Traverso et al., "Microneedles for drug delivery via the gastrointestinal tract." J. Pharm. Sci., Feb. 2015, vol. 104, No. 2, pp. 362-367. Published online Sep. 22, 2014.
Várkonyi et al., "Mono-monostatic Bodies: the Answer to Arnold's Question," Math. Intell., Sep. 2006, vol. 28, No. 4, p. 34-38.
Várkonyi et al., "Static Equilibria of Rigid Bodies: Dice, Pebbles, and the Poincaré-Hopf Theorem. J." Nonlinear Sci., Jun. 2006, vol. 16, pp. 255-281. Online publication May 22, 2006.
Vassallo et al., "Measurement of axial forces during emptying from the human stomach." Am J Physiol. Aug. 1992, vol. 263, no. 2, Pt 1, pp. G230-9.
Vazharov, "Perforation as a complication of the diagnostic upper and lower endoscopy of the gastrointestinal tract." J. IMAB—Annual Proceeding (Scientific Papers), Aug. 2012, vol. 18, No. 3, p. 273-275.
Vintner et al., "Insulin analog with additional disulfide bond has increased stability and preserved activity." Protein Sci., Mar. 2013, vol. 22, No. 3, pp. 296-305. Published online Dec. 26, 2012.
Wallace et al., "The cellular and molecular basis of gastric mucosal defense." FASEB J, May 1996, vol. 10, No. 7, pp. 731-740.
Wang et al., "Recent advances in the design of polymeric microneedles for transdermal drug delivery and biosensing." Lab Chip, Apr. 2017, vol. 17, No. 8, pp. 1373-1387.
Wiesner et al., "Normal colonic wall thickness at CT and its relation to colonic distension." J Comput Assist Tomogr, Jan.-Feb. 2002, vol. 26, no. 1, pp. 102-106.
Yoshida et al., "Complexation hydrogels as potential carriers in oral vaccine delivery systems." Eur J Pharm Biopharm., Mar. 2017, vol. 112, pp. 138-142. Available online Nov. 27, 2016.
Zhang et al., Systematic review: applications and future of gastric electrical stimulation. Aliment Pharmacol Ther., Oct. 2006, vol. 24, No. 7, pp. 991-1002.
Kim et al., "Microneedles for drug and vaccine delivery" Adv. Drug Deliv. Rev., Nov. 2012, vol. 64, No. 14, pp. 1547-1568. Available online May 1, 2012.
Koetting et al., "pH-responsive and enzymatically-responsive hydrogel microparticles for the oral delivery of therapeutic proteins: Effects of protein size, crosslinking density, and hydrogel degradation on protein delivery". J. Control. Release, Jan. 2016, vol. 221, pp. 18-25. Available online Dec. 2, 2015.
Lee et al., "Bioadhesive-Based Dosage Forms: The Next Generation". J Pharm Sci. Jul. 2000, vol. 89, No. 7, pp. 850-866.
Miller et al., "The cost of unsafe injections." Bull World Health Organ., 1999, vol. 77, No. 10, pp. 808-811.
Rao, "Rheology of Fluid and Semisolid Foods Principles and Applications." Second Edition, Springer US., 2007, book, 491 pages.

(56) References Cited

OTHER PUBLICATIONS

Steffe, "Rheological Methods in Food Process Engineering." Second Edition, Freeman Press, 1996, book, 428 pages.
Goffredo et al., "A smart pill for drug delivery with sensing capabilities," 2015 37th Annual International Conference of the IEEE Engineering in Medicine and Biology Society (EMBC), Milan, Aug. 2015, pp. 1361-1364.
Banerjee et al., "Intestinal mucoadhesive devices for oral delivery of insulin." Bioeng Transl Med., Sep. 2016, vol. 1, No. 3, pp. 338-346. Published online Aug. 19, 2016.
International Search Report and Written Opinoin dated Jul. 30, 2018 for Application No. PCT/US2018/033210 (16 pages).
International Search Report and Written Opinion dated Jul. 30, 2018 for Application No. PCT/US2018/033183 (17 pages).
International Search Report and Written Opinion dated Sep. 21, 2018 for Application No. PCT/US2018/033187 (15 pages).
International Search Report and Written Opinion dated Aug. 10, 2018 for Application No. PCT/US2018/033204 (16 pages).
International Search Report and Written Opinion dated Oct. 15, 2018 for Application No. PCT/US2018/033193 (19 pages).
International Search Report and Written Opinion dated Jul. 30, 2018 for Application No. PCT/US2018/033217 (13 pages).
International Search Report and Written Opinion dated Apr. 8, 2020 for Application No. PCT/EP2020/052521 (10 pages).
International Search Report and Written Opinion dated May 12, 2020 for Application No. PCT/US2020/016807 (11 pages).
U.S. Appl. No. 16/614,083, filed Nov. 15, 2019, by Traverso et al.
U.S. Appl. No. 16/614,177, filed Nov. 15, 2019, by Traverso et al.
U.S. Appl. No. 16/614,229, filed Nov. 15, 2019, by Traverso et al.
U.S. Appl. No. 16/613,766, filed Nov. 14, 2019, by Traverso, et al.

* cited by examiner

METHODS FOR MANUFACTURING TISSUE INTERFACING COMPONENTS

FIELD

The present disclosure generally relates to methods for manufacturing tissue interfacing components, such as needles comprising one or more therapeutic agents.

BACKGROUND

The gastrointestinal (GI) tract offers an incredible opportunity for diagnosing and treating patients. The development of smart dosage systems and articles to enable this has witnessed significant growth over the preceding decade. One of the most significant challenges in maximizing delivery and interaction with the mucosa is ensuring juxtaposition between an article and/or dosing system and the GI mucosa. Prior attempts at doing this have included the introduction of mucoadhesives as well as texturing of one side of a 2 sided system. Orally ingested drugs generally diffuse through the GI tract tissue walls in order to enter the blood stream. Typical ingested pills or articles release their cargo into the GI tract randomly and allow it to move via convection and diffusion to the tissue wall. However, many biologic drugs such as insulin cannot move through the liquid in the GI tract because they will be, for example, degraded by enzymes, even if housed in a solid formulation.

Additionally, many pharmaceutical drug formulations on the market require administration via an injection, including numerous vaccines, RNA, and peptides. Injections traditionally involve the use of a liquid formulation passing through a hollow needle and entering into the body intravenously or intramuscularly. However, these liquid formulations can cause the active pharmaceutical ingredient (API) to become unstable and thus may require refrigeration and/or increase the bulk of the dose significantly because of the required dilution.

SUMMARY

In one embodiment, a method of forming a tissue interfacing component comprises depositing a first granular therapeutic agent into a mold cavity of a mold. The mold cavity defines an elongated shape extending along a longitudinal axis from an opening of the mold cavity to a distal tip at a distal end of the mold cavity within the mold, and the distal tip is sized and shaped to facilitate insertion into tissue. The method further comprises compressing the first granular therapeutic agent within the mold along a direction oriented towards the distal end, forming a tissue interfacing component from the first granular therapeutic agent, at least in part, due to compression of the first granular therapeutic agent within the mold, and removing the tissue interfacing component from the mold cavity.

In another embodiment, a method of forming a tissue interfacing component comprises depositing a first granular therapeutic agent into a mold and applying a pressure to at least a portion of the first granular therapeutic agent of greater than or equal to 20 MPa to compress the first granular therapeutic agent and form the tissue interfacing component. The therapeutic agent comprises greater than or equal to 80 wt % of the total tissue interfacing component weight, and the tissue interfacing component is configured to penetrate at least 1 mm into human gastrointestinal mucosal tissue with a force of less than or equal to 5 N.

It should be appreciated that the foregoing concepts, and additional concepts discussed below, may be arranged in any suitable combination, as the present disclosure is not limited in this respect. Further, other advantages and novel features of the present disclosure will become apparent from the following detailed description of various non-limiting embodiments when considered in conjunction with the accompanying figures. In cases where the present specification and a document incorporated by reference include conflicting and/or inconsistent disclosure, the present specification shall control.

BRIEF DESCRIPTION OF THE DRAWINGS

Non-limiting embodiments of the present invention will be described by way of example with reference to the accompanying figures, which are schematic and are not intended to be drawn to scale. In the figures, each identical or nearly identical component illustrated is typically represented by a single numeral. For purposes of clarity, not every component is labeled in every figure, nor is every component of each embodiment of the invention shown where illustration is not necessary to allow those of ordinary skill in the art to understand the invention. In the figures.

DETAILED DESCRIPTION

Figure 1:
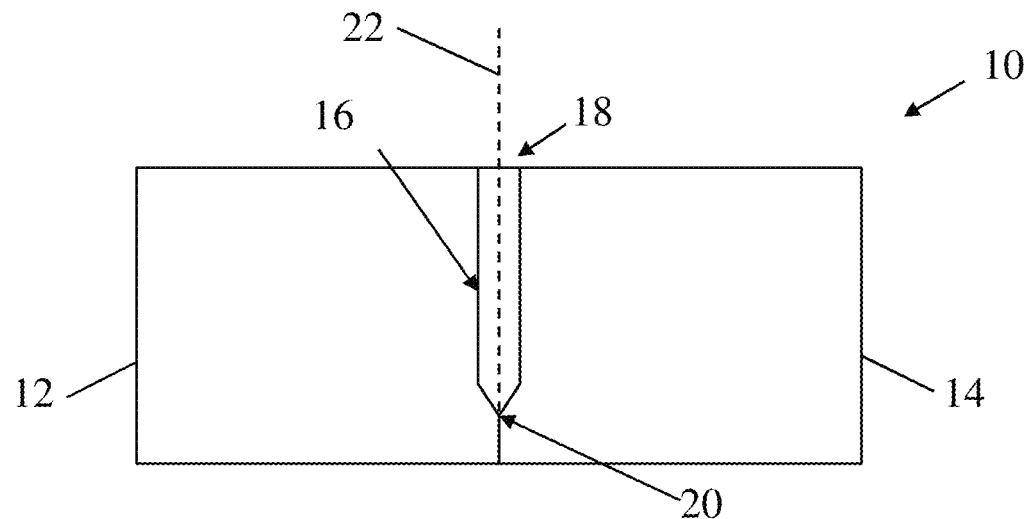
FIG. 1 is a schematic representation of a mold for forming a tissue interfacing component, according to some embodiments.

The inventors have recognized and appreciated numerous benefits associated with tissue interfacing components comprising an active pharmaceutical ingredient (API) or other therapeutic agents that may be injected or otherwise physically inserted into tissue. For example, some biological therapeutic products (e.g., peptides or larger molecules) may not be well absorbed from the gastric cavity (e.g., after oral ingestion). To increase the absorption of such products, the therapeutic agent may be physically deposited into mucosal tissue (e.g., surrounding the stomach) or other suitable tissue. Accordingly, the inventors have recognized and appreciated numerous benefits associated with methods for manufacturing tissue interfacing components containing APIs that are constructed and arranged to be inserted into tissue (e.g., mucosal tissue) and subsequently release the APIs into the tissue for absorption. As used herein, the term "therapeutic agent" (also referred to as a "drug", "active pharmaceutical ingredient", or similar term) refers to an agent that is administered to a subject to treat a disease, disorder, or other clinically recognized condition, or for prophylactic purposes, and has a clinically significant effect on the body of the subject to treat and/or prevent the disease, disorder, or condition. Further, these terms may be used interchangeably in the various embodiments as the disclosure is not limited to any particular type of therapeutic agent.

In some embodiments, a tissue interfacing component may be configured as an elongated structure (e.g., an elongated cylindrical or prismatic structure) and the tissue interfacing component may have a pointed distal tip, which may facilitate penetration of the tissue interfacing component into tissue, such as mucosal tissue or other suitable tissue. Accordingly, in some embodiments, the tissue interfacing component may be described herein as a needle or similar elongated structure that may be injected into tissue, and after injection, the needle may at least partially dissolve and release one or more APIs and/or other therapeutic agents into the tissue.

According to some aspects, methods for manufacturing a tissue interfacing component may comprise compressing a granular material within a mold. For example, a granular therapeutic agent and/or other granular material (e.g., a powdered API or drug or other suitable powdered or granular material) may be deposited or otherwise loaded into a mold cavity of a mold. The mold cavity may define a longitudinal axis extending from an opening of the mold cavity to distal tip positioned at a distal end of the mold cavity, and the distal tip of the mold cavity may be closed within the mold. Accordingly, the mold cavity may be referred to herein as a blind hold or blind cavity. After loading the granular therapeutic agent, the granular therapeutic agent may be compressed within the mold cavity along a direction oriented substantially along the longitudinal axis and towards the distal tip, and a tissue interfacing component. A solid or substantially solid tissue interfacing component may be formed within the mold cavity, at least in part, due to the compression of the granular therapeutic agent. In some embodiments, such compression of the granular therapeutic agent may be achieved with a mold punch. For example, a mold punch may be inserted into the opening of the mold cavity, and the mold punch may be moved towards the distal end of the mold cavity to compress and compact the granular therapeutic agent within the mold cavity and form a solid tissue interfacing component. In this manner, a compressive force applied by the mold punch to form the tissue interfacing component from the granular therapeutic agent may be directed substantially along a longitudinal axis of the tissue interfacing component. For example, as noted above, in some embodiments a tissue interfacing component may be formed as a needle, and thus, the compressive force applied by the mold punch may be applied along the longitudinal axis of the needle towards the needle tip.

After compressing the therapeutic agent in the mold, thereby forming the tissue interfacing component in some instances, the tissue interfacing component may be removed from the mold. In some embodiments, the mold may be constructed and arranged to facilitate such removal of the tissue interfacing component. For example, in some embodiments, the mold may be formed from corresponding first and second mold portions that may be coupled to one another to form the mold cavity. For example, each mold portion may comprise wall portions that define the mold cavity when the mold portions are coupled. In some embodiments, the mold portions may be separable along a plane that is substantially parallel to the longitudinal axis of the tissue interfacing component. For instance, wall portions of each mold portion may be configured to define approximately half of the tissue interfacing component when the mold portions are coupled to one another with a parting line that is appropriately aligned with the geometry of the resulting formed tissue interfacing component to allow the mold portions to be separated and to allow removal of the tissue interfacing component.

As used herein, a granular material generally refers to a material such as a powdered material comprising a plurality of discrete solid granules or particles that may be compressed and compacted to form a substantially solid mass. For example, granular therapeutic agents may comprise powdered drugs or other powdered APIs that may be compacted within a mold to form a solid drug-containing component.

As noted above, in some embodiments, a tissue interfacing component may be formed as a needle or other elongated structure having a pointed distal tip. In some embodiments, the mold cavity may be configured to form such features when a granular therapeutic agent is compressed within a mold cavity. For example, the distal end of the mold cavity opposite the opening of the mold cavity may have a shape corresponding to the desired geometry. When the granular therapeutic agent is compressed with the mold punch, the granular therapeutic agent may conform to the geometry of the mold cavity to form a solid tissue interfacing component with a desired distal tip geometry configured to facilitate insertion into tissue (e.g., a pointed tip or other suitable geometry).

In some embodiments, multiple granular materials may be deposited into a mold cavity to form a tissue interfacing component. For example, a first granular material (e.g., a granular therapeutic agent) may be deposited into the mold cavity first to form a distal portion of the tissue interfacing component, and a second granular material (e.g., a second granular therapeutic agent or other granular material) may subsequently be deposited into the mold cavity to form a proximal portion of the tissue interfacing components. The first and second granular material may be compressed together with the mold punch to compact and solidify the first and second granular materials, thereby forming the tissue interfacing component. However, embodiments in which the first and second granular materials are compressed in separate compression steps are also contemplated as the disclosure is not so limited. In some embodiments, such arrangements may allow a desired therapeutic agent to be localized to a distal portion of the tissue interfacing component for dissolution after being injected or otherwise inserted into tissue, and the second granular material may provide structural support to the tissue interfacing component to facilitate insertion into tissue.

In some embodiments, a tissue interfacing component may comprise a relatively high loading of active pharmaceutical ingredients (e.g., drugs or other therapeutic agents). In certain embodiments, the tissue interfacing component may be formed entirely from a therapeutic agent (e.g., API) such that the therapeutic agent comprises about 100% of the weight of the tissue interfacing component. In other embodiments, a granular therapeutic agent from which a tissue interfacing component is formed comprises a solid therapeutic agent (e.g., a solid API) and, optionally, a support material (e.g., a binder such as a polymer) such that the solid therapeutic agent is present in the component in a relatively high amount (e.g., greater than or equal to 80 wt %) versus the total weight of the tissue interfacing component. Such tissue-interfacing components with high loading of therapeutic agents may be useful for delivery of API doses (e.g., to a subject). Advantageously, in some embodiments, the reduction of volume for delivering a desired API dose as compared to a liquid formulation may permit the creation of solid needle delivery systems for a wide variety of drugs in a variety of places/tissues (e.g., tongue, GI mucosal tissue, skin). The disclosed structures may also reduce and/or eliminate the application of an external force in order to inject a drug solution through the small opening in the needle. In some cases, a physiologically relevant dose may be present in a single tissue interfacing component (e.g., having a relatively high API loading).

Depending on the particular embodiment, a mold punch, and associated actuation system, or other appropriate system may be constructed and arranged to apply any suitable amount of pressure to compress and compact a granular therapeutic agent to form a solid tissue interfacing component. For example, in some embodiments, the tissue-interfacing component is formed using at least 1 MPa of pressure, at least 2 MPa of pressure, at least 3 MPa of pressure, at least 5 MPa of pressure, at least 7 MPa of pressure, at least 10 MPa of pressure, at least 12 MPa of pressure, at least 15 MPa of pressure, at least 20 MPa of pressure, at least 25 MPa of pressure, at least 30 MPa of pressure, at least 40 MPa of pressure, at least 50 MPa of pressure, at least 75 MPa of pressure, at least 150 MPa of pressure, at least 300 MPa of pressure, at least 600 MPa of pressure, at least 900 MPa of pressure, at least 1 GPa of pressure, or at least 1.2 GPa of pressure. In some embodiments, the tissue-interfacing component is formed using less than or equal to 1.4 GPa of pressure, less than or equal to 1.2 GPa of pressure, less than or equal to 1 GPa of pressure, less than or equal to 900 MPa of pressure, less than or equal to 600 MPa of pressure, less than or equal to 300 MPa of pressure, less than or equal to 150 MPa of pressure, less than or equal to 100 MPa of pressure, less than or equal to 75 MPa of pressure, less than or equal to 50 MPa of pressure, less than or equal to 40 MPa of pressure, less than or equal to 30 MPa of pressure, less than or equal to 25 MPa of pressure, less than or equal to 20 MPa of pressure, less than or equal to 15 MPa of pressure, less than or equal to 12 MPa of pressure, less than or equal to 10 MPa of pressure, less than or equal to 7 MPa of pressure, less than or equal to 5 MPa pressure, less than or equal to 3 MPa of pressure, or less than or equal to 2 MPa of pressure. Combinations of the above-referenced ranges are also possible (e.g., at least 1 MPa of pressure and less than or equal to 100 MPa of pressure, at least 20 MPa of pressure and less than or equal to 100 MPa of pressure, at least 100 MPa and less than or equal to 1.4 GPa of pressure). In some embodiments, an applied pressure may be between about 25 MPa and about 1000 MPa. Other ranges are also possible.

In some embodiments, the tissue-interfacing component has a particular largest dimension (e.g., length). In certain embodiments, the length of the tissue interfacing component may be between about 1 mm and about 10 mm (e.g., between about 1.5 mm and about 8 mm). In some embodiments, the length is greater than or equal to 1 mm, greater than or equal to 2 mm, greater than or equal to 3 mm, greater than or equal to 5 mm, greater than or equal to 7 mm, or greater than or equal to 10 mm. In some embodiments, the largest dimension of the tissue interfacing component is less than or equal to 10 mm, less than or equal to 7 mm, less than or equal to 5 mm, less than or equal to 3 mm, less than or equal to 2 mm, or less than or equal to 1.5 mm. Combinations of the above-referenced ranges are also possible, though dimensions both greater and less than those noted above are also contemplated.

In certain embodiments, the tissue-interfacing component has an average cross-sectional dimension that is perpendicular relative to a largest dimension of the component (e.g., a diameter) between about 0.5 mm and about 2 mm (e.g., between about 0.8 mm and 1.6 mm). In some embodiments, the diameter may be greater than or equal to 0.5 mm, greater than or equal to 0.6 mm, greater than or equal to 0.7 mm, greater than or equal to 0.8 mm, greater than or equal to 0.9 mm, greater than or equal to 1 mm, greater than or equal to 1.1 mm, greater than or equal to 1.2 mm, greater than or equal to 1.3 mm, greater than or equal to 1.4 mm, greater than or equal to 1.6 mm, or greater than or equal to 1.8 mm. In some embodiments, the tissue-interfacing component has an average cross-sectional dimension of less than or equal to 2.0 mm, less than or equal to 1.9 mm, less than or equal to 1.7 mm, less than or equal to 1.5 mm, less than or equal to 1.4 mm, less than or equal to 1.3 mm, less than or equal to 1.2 mm, less than or equal to 1.1 mm, less than or equal to 1 mm, less than or equal to 0.9 mm, less than or equal to 0.8 mm, less than or equal to 0.7 mm, or less than or equal to 0.6, or less than or equal to 0.5 mm. Combinations of the above-referenced ranges are also possible (e.g., greater than or equal to 0.5 mm and less than or equal to 2.0 mm). Other ranges are also possible.

According to some aspects of the present disclosure, tissue interfacing components manufactured using the methods described herein may be administered via a device that may be ingested by a patient. In some embodiments, the device may be a self-righting article, which may be configured such that the article may orient itself relative to a surface (e.g., a surface of a tissue of a subject). The self-righting articles described herein may comprise one or more tissue engaging surfaces configured to engage (e.g., interface with, inject into, anchor) with a surface (e.g., a surface of a tissue of a subject). For example, the self-righting article may be placed at any orientation proximate a surface and the self-righting article will (re)-orient itself such that the tissue engaging surface is in contact (e.g., direct contact) with the surface. In some embodiments, the self-righting article may have a particular shape and/or distribution of density (or mass) which, for example, enables the self-righting behavior of the article. In some such embodiments, the capsule containing the self-righting article may be administered to a subject (e.g., for delivery of the self-righting article to a location internal of the subject such as the gastrointestinal tract). In some embodiments, the self-righting may comprise a tissue interfacing component and/or a pharmaceutical agent (e.g., for delivery of the active pharmaceutical agent to a location internal of the subject). In some cases, upon contact of the tissue with the tissue engaging surface of the article, the self-righting article may be configured to release one or more tissue interfacing components. In some cases, the tissue interfacing component is associated with a self-actuating component. For example, the self-righting article may comprise a self-actuating component configured, upon exposure to a fluid, to release the tissue interfacing component from the self-righting article. In some cases, the tissue interfacing component may comprise and/or be associated with the pharmaceutical agent (e.g., for delivery to a location internal to a subject).

In some cases, the tissue interfacing component may be configured to penetrate a particular depth into human gastrointestinal mucosal tissue at a particular force. For example, the tissue interfacing component may be configured to penetrate greater than or equal to 1 mm (e.g., greater than or equal to 2 mm, greater than or equal to 3 mm, greater than or equal to 4 mm, or greater than or equal to 5 mm) with a force of less than or equal to 30 N (e.g., less than or equal to 30 N, less than or equal to 20 N, less than or equal to 10 N, or less than or equal to 5 N. In certain embodiments, the penetration force may be between about 6 N and about 30 N. Of course, penetration depths and forces both greater and less than those noted above are also contemplated as the disclosure is not so limited.

In some cases, a tissue interfacing component may be configured to deliver a particular amount of active pharmaceutical agent per square centimeter of tissue of a subject. For example, in some embodiments, the tissue interfacing component is configured to deliver greater than or equal to 0.01 µg, greater than or equal to 0.05 µg, greater than or equal to 0.1 µg, greater than or equal to 0.2 µg, greater than or equal to 0.5 µg, greater than or equal to 0.7 µg, greater than or equal to 1 µg, greater than or equal to 2 µg, greater than or equal to 5 µg, or greater than or equal to 10 µg of pharmaceutical agent per square centimeter of tissue of the subject proximate the penetration location of the tissue interfacing component. In certain embodiments, the tissue interfacing component is configured to deliver less than or equal to 20 µg, less than or equal to 5 µg, less than or equal to 2 µg, less than or equal to 1 µg, less than or equal to 0.7 µg, less than or equal to 0.5 µg, less than or equal to 0.2 µg, less than or equal to 0.1 µg, or less than or equal to 0.05 µg of pharmaceutical agent per square centimeter of tissue. Combinations of the above-referenced ranges are also possible (e.g., greater than or equal to 1 µg and less than or equal to 20 µg). In some embodiments, the tissue interfacing component is configured to deliver greater than or equal to 1 µg of pharmaceutical agent per square centimeter of tissue of the subject over any suitable time period (e.g., in greater than or equal to 0.1 seconds, in greater than or equal to 0.5 seconds, in greater than or equal to 1 second, in greater than or equal to 5 seconds, in greater than or equal to 30 seconds, greater than or equal to 1 minute, greater than or equal to 5 minutes, 10 minutes, greater than or equal to 30 minutes, greater than or equal to 1 hour, greater than or equal to 4 hours, greater than or equal to 24 hours, greater than or equal to 48 hours, greater than or equal to 72 hours, greater than or equal to 96 hours, greater than or equal to 120 hours, greater than or equal to 144 hours, greater than or equal to 168 hours). Of course delivery of doses both greater and less than those noted above overtime periods different than those noted above are also contemplated as the disclosure is not limited to any particular dosage and/or time period.

In certain embodiments, the tissue interfacing component comprises a binder. Non-limiting examples of suitable binders include sugar such as sorbitol and sucrose, gelatin, polymers such as polyvinyl alcohol (PVA), polyethylene glycol (PEG), polycaprolactone (PCL), and polyvinylpyrrolidone (PVP), and polymers comprising ethanol or other Class 3 organic solvents (e.g., acetic acid, heptane, acetone, formic acid, isobutyl acetate, etc.).

In an exemplary embodiment, a tissue interfacing component comprises greater than or equal to 80 wt % solid active pharmaceutical agent versus the total article weight. In certain embodiments, the tissue interfacing component comprises greater than or equal to 1 mg of active pharmaceutical agent. According to some embodiments, the pharmaceutical agent is selected from the group consisting of bacteriophage, DNA, mRNA, insulin, human growth hormone, monoclonal antibodies, adalimumab, epinephrine, and ondansetron. In certain exemplary embodiments, the active pharmaceutical agent is cast into a mold to form the tissue interfacing component. In some embodiments, the mold is centrifuged. According to certain embodiments, the tissue interfacing component further comprises a binder. In certain embodiments, the binder comprises sugar such as sorbitol or sucrose, gelatin, polymer such as PVA, PEG, PCL, PVA, or PVP, and/or ethanol. According to certain embodiments, the tissue interfacing component has a Young's elastic modulus of greater than or equal to 100 MPa. In some embodiments, the tissue interfacing component is configured to penetrate at least 1 mm into human gastrointestinal mucosal tissue with a force of less than or equal to 20 mN. According to certain embodiments, the tissue interfacing component is configured to deliver at least 1 mg of pharmaceutical agent per square centimeter of a tissue of a subject, and/or the tissue interfacing component comprises greater than or equal to 1 mg of active pharmaceutical agent per square centimeter.

In one specific non-limiting embodiment, a method of forming a tissue interfacing component includes introducing, into a mold, a composition comprising greater than 80 wt % solid pharmaceutical agent versus the total weight of the composition, applying greater than or equal to 1 MPa of pressure to the composition, and heating the composition to a temperature of at least 70° C. for at least 1 minute.

According to some embodiments, the methods described herein are compatible with one or more therapeutic agents, such as drugs, nutrients, microorganisms, in vivo sensors, and tracers. In some embodiments, the therapeutic agent, is a pharmaceutical, biological, nutraceutical, prophylactic, diagnostic, contrast (i.e. for imaging), or any other appropriate agent which may be injected into a subject's body. While much of the specification describes the use of active pharmaceutical ingredients, it should be understood that any desired therapeutic agent for any appropriate application may be used as the disclosure is not so limited.

Therapeutic agents can include, but are not limited to, any synthetic or naturally-occurring biologically active compound or composition of matter which, when administered to a subject (e.g., a human or nonhuman animal), induces a desired pharmacologic, immunogenic, and/or physiologic effect by local and/or systemic action. For example, useful or potentially useful within the context of certain embodiments are compounds or chemicals traditionally regarded as drugs, vaccines, and biopharmaceuticals, Certain such agents may include molecules such as proteins, peptides, hormones, nucleic acids, gene constructs, etc., for use in therapeutic, diagnostic, and/or enhancement areas, including, but not limited to medical or veterinary treatment, prevention, diagnosis, and/or mitigation of disease or illness (e.g., HMG co-A reductase inhibitors (statins) like rosuvastatin, nonsteroidal anti-inflammatory drugs like meloxicam, selective serotonin reuptake inhibitors like escitalopram, blood thinning agents like clopidogrel, steroids like prednisone, antipsychotics like aripiprazole and risperidone, analgesics like buprenorphine, antagonists like naloxone, montelukast, and memantine, cardiac glycosides like digoxin, alpha blockers like tamsulosin, cholesterol absorption inhibitors like ezetimibe, metabolites like colchicine, antihistamines like loratadine and cetirizine, opioids like loperamide, proton-pump inhibitors like omeprazole, anti(retro) viral agents like entecavir, dolutegravir, rilpivirine, and cabotegravir, antibiotics like doxycycline, ciprofloxacin, and azithromycin, anti-malarial agents, and synthroid/levothyroxine); substance abuse treatment (e.g., methadone and varenicline); family planning (e.g., hormonal contraception); performance enhancement (e.g., stimulants like caffeine); and nutrition and supplements (e.g., protein, folic acid, calcium, iodine, iron, zinc, thiamine, niacin, vitamin C, vitamin D, and other vitamin or mineral supplements).

In certain embodiments, as used herein, a term "therapeutic agent" or also referred to as a "drug" or "active pharmaceutical ingredient" refers to an agent that is administered to a subject to treat a disease, disorder, or other clinically recognized condition, or for prophylactic purposes, and has a clinically significant effect on the body of the subject to treat and/or prevent the disease, disorder, or condition. Listings of examples of known therapeutic agents can be found, for example, in the United States Pharmacopeia (USP), Goodman and Gilman's The Pharmacological Basis of Therapeutics, 10th Ed., McGraw Hill, 2001; Katzung, B. (ed.) Basic and Clinical Pharmacology, McGraw-Hill/Appleton & Lange; 8th edition (Sep. 21, 2000); Physician's Desk Reference (Thomson Publishing), and/or The Merck Manual of Diagnosis and Therapy, 17th ed. (1999), or the 18th ed (2006) following its publication, Mark H. Beers and Robert Berkow (eds.), Merck Publishing Group, or, in the case of animals, The Merck Veterinary Manual, 9th ed., Kahn, C. A. (ed.), Merck Publishing Group, 2005; and "Approved Drug Products with Therapeutic Equivalence and Evaluations," published by the United States Food and Drug Administration (F.D.A.) (the "Orange Book"). Examples of drugs approved for human use are listed by the FDA under 21 C.F.R. §§ 330.5, 331 through 361, and 440 through 460, incorporated herein by reference; drugs for veterinary use are listed by the FDA under 21 C.F.R. §§ 500 through 589, incorporated herein by reference. In certain embodiments, the therapeutic agent is a small molecule. Exemplary classes of therapeutic agents include, but are not limited to, analgesics, anti-analgesics, anti-inflammatory drugs, antipyretics, antidepressants, antiepileptics, antipsychotic agents, neuroprotective agents, anti-proliferatives, such as anti-cancer agents, antihistamines, antimigraine drugs, hormones, pro staglandins, antimicrobials (including antibiotics, antifungals, antivirals, antiparasitics), antimuscarinics, anxioltyics, bacteriostatics, immunosuppressant agents, sedatives, hypnotics, antipsychotics, bronchodilators, anti-asthma drugs, cardiovascular drugs, anesthetics, anti-coagulants, inhibitors of an enzyme, steroidal agents, steroidal or non-steroidal anti-inflammatory agents, corticosteroids, dopaminergics, electrolytes, gastro-intestinal drugs, muscle relaxants, nutritional agents, vitamins, parasympathomimetics, stimulants, anorectics and anti-narcoleptics. Nutraceuticals can also be incorporated into the drug delivery device. These may be vitamins, supplements such as calcium or biotin, or natural ingredients such as plant extracts or phytohormones.

In some embodiments, the therapeutic agent is one or more antimalarial drugs. Exemplary antimalarial drugs include quinine, lumefantrine, chloroquine, amodiaquine, pyrimethamine, proguanil, chlorproguanil-dapsone, sulfonamides such as sulfadoxine and sulfamethoxypyridazine, mefloquine, atovaquone, primaquine, halofantrine, doxycycline, clindamycin, artemisinin and artemisinin derivatives. In some embodiments, the antimalarial drug is artemisinin or a derivative thereof. Exemplary artemisinin derivatives include artemether, dihydroartemisinin, arteether and artesunate. In certain embodiments, the artemisinin derivative is artesunate.

In another embodiment, a therapeutic agent is an immunosuppressive agent. Exemplary immunosuppressive agents include glucocorticoids, cytostatics (such as alkylating agents, antimetabolites, and cytotoxic antibodies), antibodies (such as those directed against T-cell recepotors or Il-2 receptors), drugs acting on immunophilins (such as cyclosporine, tacrolimus, and sirolimus) and other drugs (such as interferons, opioids, TNF binding proteins, mycophenolate, and other small molecules such as fingolimod).

In certain embodiments, a therapeutic agent is a hormone or derivative thereof. Non-limiting examples of hormones include insulin, growth hormone (e.g., human growth hormone), vasopressin, melatonin, thyroxine, thyrotropin-releasing hormone, glycoprotein hormones (e.g., luteinizing hormone, follicle-stimulating hormone, thyroid-stimulating hormone), eicosanoids, estrogen, progestin, testosterone, estradiol, cortisol, adrenaline, and other steroids.

In some embodiments, a therapeutic agent is a small molecule drug having molecular weight less than about 2500 Daltons, less than about 2000 Daltons, less than about 1500 Daltons, less than about 1000 Daltons, less than about 750 Daltons, less than about 500 Daltons, less or than about 400 Daltons. In some cases, the therapeutic agent is a small molecule drug having molecular weight between 200 Daltons and 400 Daltons, between 400 Daltons and 1000 Daltons, or between 500 Daltons and 2500 Daltons.

In some embodiments, a therapeutic agent is selected from the group consisting of active pharmaceutical agents such as insulin, nucleic acids, peptides, bacteriophage, DNA, mRNA, human growth hormone, monoclonal antibodies, adalimumab, epinephrine, GLP-1 Receptor agonists, semaglutide, liraglutide, dulaglitide, exenatide, factor VIII, small molecule drugs, progrstin, vaccines, subunit vaccines, recombinant vaccines, polysaccharide vaccines, and conjugate vaccines, toxoid vaccines, influenza vaccine, shingles vaccine, prevnar pneumonia vaccine, mmr vaccine, tetanus vaccine, hepatitis vaccine, HIV vaccine Ad4-env Clade C, HIV vaccine Ad4-mGag, dna vaccines, ma vaccines, etanercept, infliximab, filgastrim, glatiramer acetate, rituximab, bevacizumab, any molecule encapsulated in a nanoparticle, epinephrine, lysozyme, glucose-6-phosphate dehydrogenase, other enzymes, certolizumab pegol, ustekinumab, ixekizumab, golimumab, brodalumab, guselu,ab, secikinumab, omalizumab, tnf-alpha inhibitors, interleukin inhibitors, vedolizumab, octreotide, teriperatide, crispr cas9, insulin glargine, insulin detemir, insulin lispro, insulin aspart, human insulin, antisense oligonucleotides, and ondansetron.

In an exemplary embodiment, the therapeutic agent is insulin.

In certain embodiments, the therapeutic agent is present in the tissue interfacing component at a concentration such that, upon release from the tissue interfacing component, the therapeutic agent elicits a therapeutic response.

In some cases, the therapeutic agent may be present at a concentration below a minimal concentration generally associated with an active therapeutic agent (e.g., at a microdose concentration). For example, in some embodiments, the tissue interfacing component comprises a first therapeutic agent (e.g., a steroid) at a relatively low dose (e.g., without wishing to be bound by theory, low doses of therapeutic agents such as steroids may mediate a subject's foreign body response(s) (e.g., in response to contact by a tissue interfacing components) at a location internal to a subject). In some embodiments, the concentration of the therapeutic agent is a microdose less than or equal to 100 μg and/or 30 nMol. In other embodiments, however, the therapeutic agent is not provided in a microdose and is present in one or more amounts listed above.

In some embodiments, the tissue-interfacing component is administered to a subject (e.g., orally). In certain embodiments, the article may be administered orally, rectally, vaginally, nasally, or uretherally. In certain embodiments, the tissue-interfacing component (e.g., and/or the API contained therein) is administered by contacting the skin of a subject with the component. In an exemplary embodiment, the tissue-interfacing component (e.g., and/or the API contained therein) is administered by contacting the buccal tissue (e.g., lip, palatal area, cheek, sublingual, tongue) of a subject with the component. In yet another exemplary embodiment, the tissue-interfacing component is administered orally and, upon reaching a location internal the subject (e.g., the GI tract such as the colon, the duodenum, the ileum, the jejunum, the stomach, the buccal space, the esophagus, etc.), the tissue-interfacing component interfaces (e.g., contacts) with the tissue of the subject at the location internal the subject and at least partially penetrates the tissue. In certain embodiments, at least a portion of the tissue-interfacing component penetrates the tissue of the subject and at least a portion of the support material and/or the active pharmaceutical agent dissolves into the tissue of the subject.

Advantageously, administration of a tissue-interfacing component having a relatively high loading of API to the GI tract may permit more effective delivery of the API as compared to traditional methods. For example, without wishing to be bound by theory, delivering a drug via an injection to the GI tract has been shown to have a higher bioavailability compared to other methods.

As used herein, a "subject" refers to any animal such as a mammal (e.g., a human). Non-limiting examples of subjects include a human, a non-human primate, a cow, a horse, a pig, a sheep, a goat, a dog, a cat or a rodent such as a mouse, a rat, a hamster, a bird, a fish, or a guinea pig. Generally, the invention is directed toward use with humans. In some embodiments, a subject may demonstrate health benefits, e.g., upon administration of the self-righting article.

Turning now to the figures, specific non-limiting embodiments are described in further detail. It should be understood that the various systems, components, features, and methods described relative to these embodiments may be used either individually and/or in any desired combination as the disclosure is not limited to only the specific embodiments described herein.

FIG. 1 is a schematic side view of a mold 10 which may be used to form a tissue interfacing component, according to some embodiments. The mold includes a first mold portion 12 and a second mold portion 14 that are coupleable to each other to define a mold cavity 16 disposed between the two mold portions. The mold cavity extends along a longitudinal axis 22 from an opening 18 of the mold cavity to a distal end 20 of the mold cavity. The distal end of the mold cavity may have a distal tip geometry that is configured to mold a distal tip of the resulting tissue interfacing component that is shaped and sized to facilitate insertion into tissue. For example, as illustrated in the figure, the distal end 20 of the mold cavity may be positioned internal to the mold 10, and the distal end may define a distal tip of the mold cavity, which may be configured as a pointed tip or other suitable geometry as described herein.

Figure 2:
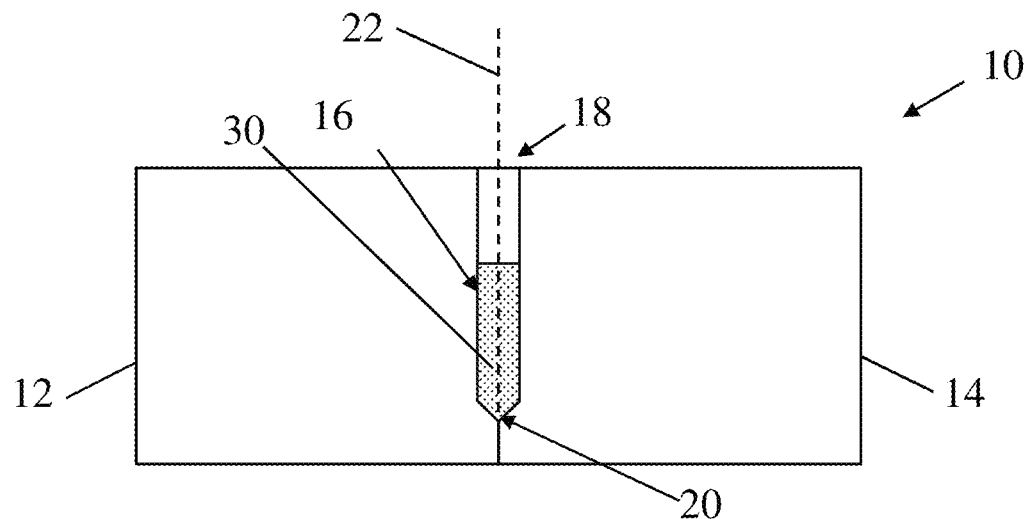
FIG. 2 is a schematic representation of the mold of FIG. 1, further illustrating a granular therapeutic agent deposited within the mold.
Figure 3:
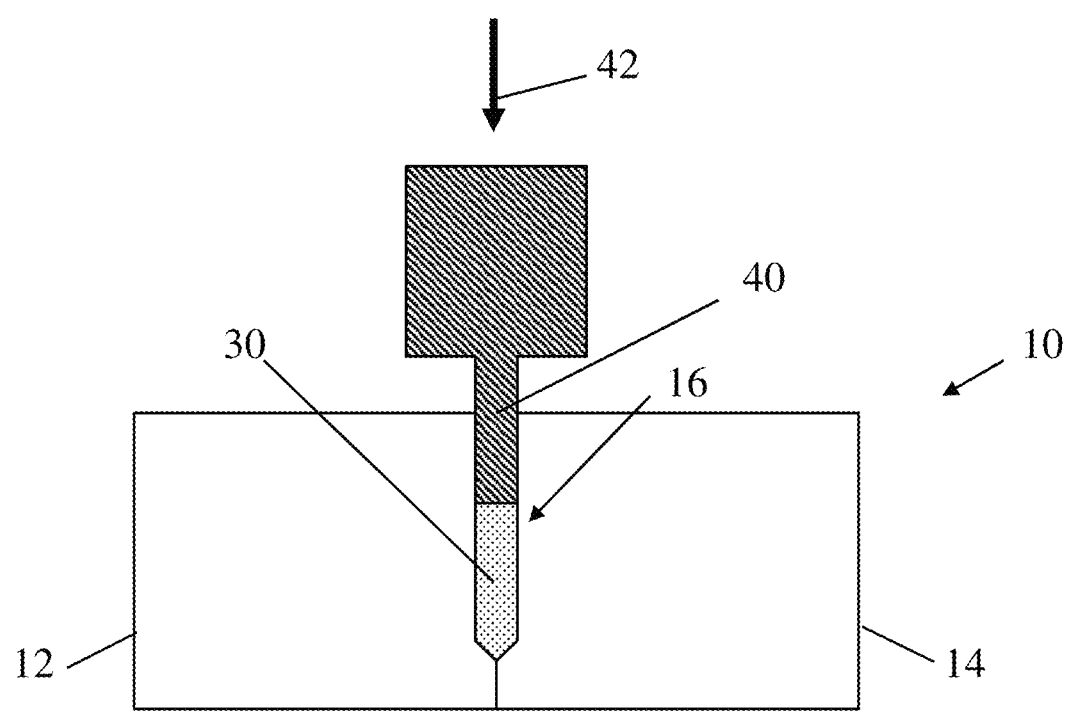
FIG. 3 is a schematic representation of the mold of FIG. 1, further illustrating a mold punch and a granular therapeutic agent received in the mold.
Figure 4:
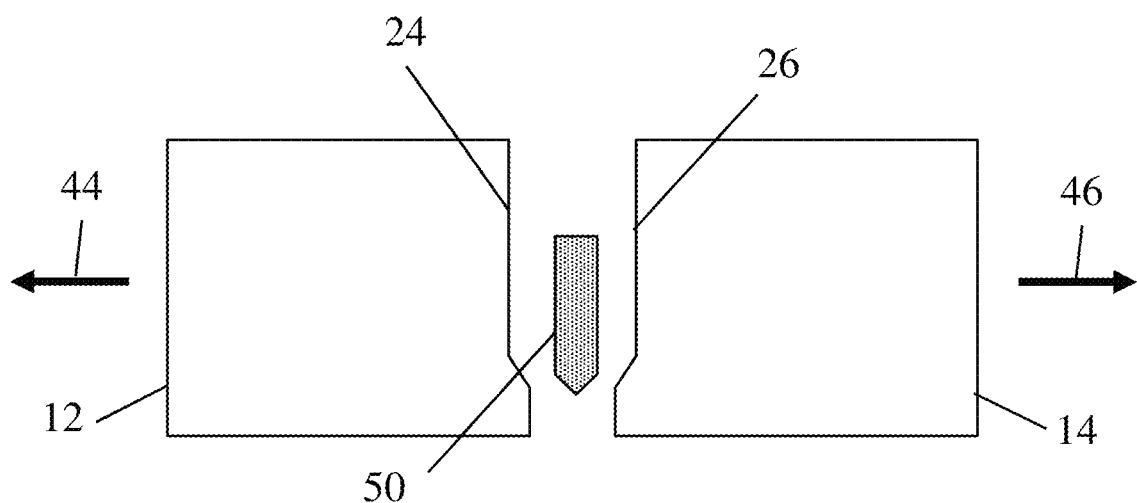
FIG. 4 is a schematic representation of the mold of FIG. 1, further illustrating separation of mold portions to remove a tissue interfacing component.

Referring to FIGS. 1-4, a granular material 30 (e.g., a granular therapeutic agent) may be deposited into the mold cavity 16 as illustrated in FIG. 2. For example, the longitudinal axis 22 may align with a vertical direction, and the granular material 30 may be deposited into the mold along this direction (e.g., via a gravity feed or by otherwise pouring or dispensing the granular material into the mold cavity 16 along the vertical direction). Once positioned in the cavity, the granular material may subsequently be compressed within the mold cavity, such as with a mold punch 40 as illustrated in FIG. 4. For example, the mold punch 40 may have a portion that is configured to be received in the opening 18 of the mold cavity 16, and the mold punch may be moved along direction 42, which may correspond to movement of the mold punch 40 along the longitudinal axis 22 towards the distal end 20 of the mold cavity 16. In this manner, the mold punch may apply a compressive force to the granular material 30 to compress and compact the granular material, thereby forming a solid tissue interfacing component 50 having a shape corresponding to a distal portion of the mold cavity 16.

Subsequently, the tissue interfacing component 50 may be removed from the mold cavity 16. For example, as illustrated in FIG. 4, in some embodiments the first and second mold portions 12 and 14 may be separable and may be moved apart from one another along directions 44 and 46, respectively, to facilitate removal of the tissue interfacing component. In some such embodiments, each of the first and first and second mold portions 12 and 14 may include wall portions 24 and 26 configured to form the mold cavity 16 when the mold portions are coupled to one another. As illustrated, the wall portions 24 and 26 may extend from the opening 18 of the mold cavity 16 to the distal end 20 of the mold cavity. Further, in some embodiments, mold portions may be separated manually and/or they may be separated automatically during a molding process using automated mold opening mechanisms such as: opening and return pins; hydraulic, pneumatic, and/or electric actuators; and/or any other appropriate mold opening mechanism. The mold may also include ejection pins in some instances to aid in the removal of a molded tissue interface component.

While a mold comprising two mold portions is depicted in FIGS. 1-4, it should be understood that other arrangements, such as molds formed from three or more mold portions coupleable to one another to form a mold cavity may be suitable. Accordingly, it should be appreciated that the current disclosure is not limited to molds comprising any particular number of mold portions.

Figure 5:
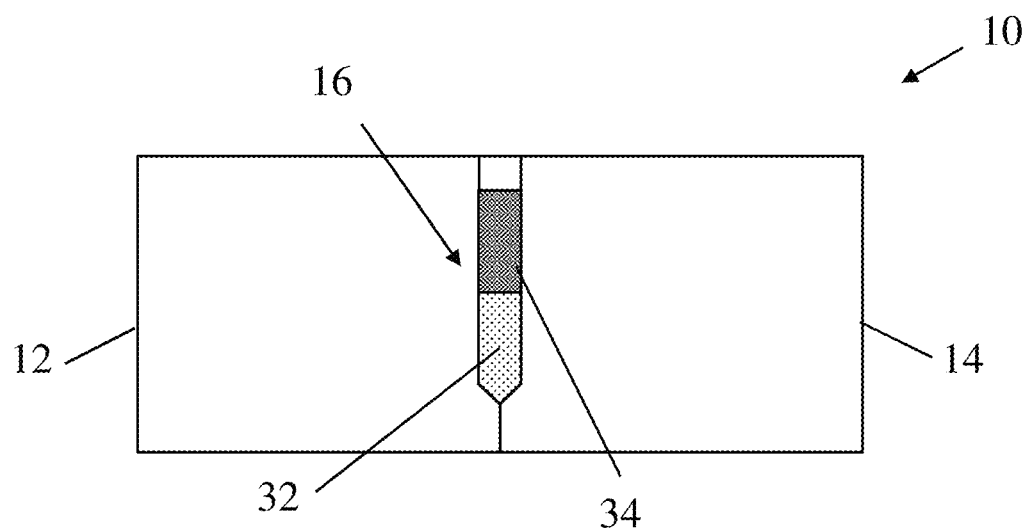
FIG. 5 is a schematic representation of the mold of FIG. 1 with two granular materials received in the mold.

As discussed above, in some embodiments, a tissue interfacing component may be formed from a single granular material (e.g., a granular therapeutic agent), or multiple granular materials. For example FIG. 5 depicts an embodiment of a mold 10 in which two different granular materials are deposited into a mold cavity 16. In particular, a first granular material 32 (e.g., a first granular therapeutic agent) may be deposited into the mold cavity first to form a distal portion of the tissue interfacing component, and a second granular material 34 (e.g., a second granular therapeutic agent or other suitable granular material) may be subsequently deposited into the mold to form a proximal portion of the tissue interfacing component. While two granular materials are depicted in FIG. 5, it should be understood that any suitable number of granular materials may be deposited in any suitable proportion to form a tissue interfacing component with a plurality of sequentially arranged portions with a corresponding number of different compositions.

Figure 6A:
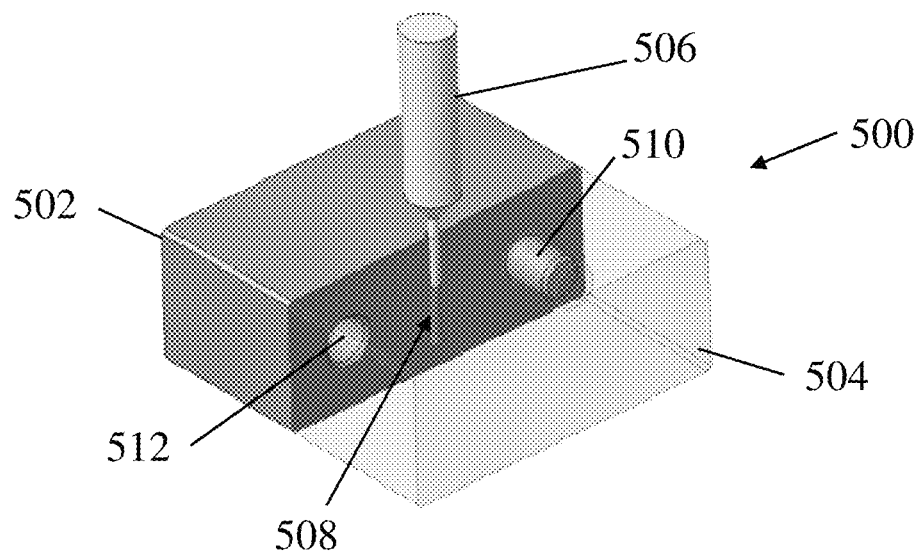
FIG. 6A is a perspective view of a mold for forming a tissue interfacing component, according to some embodiments.
Figure 6B:
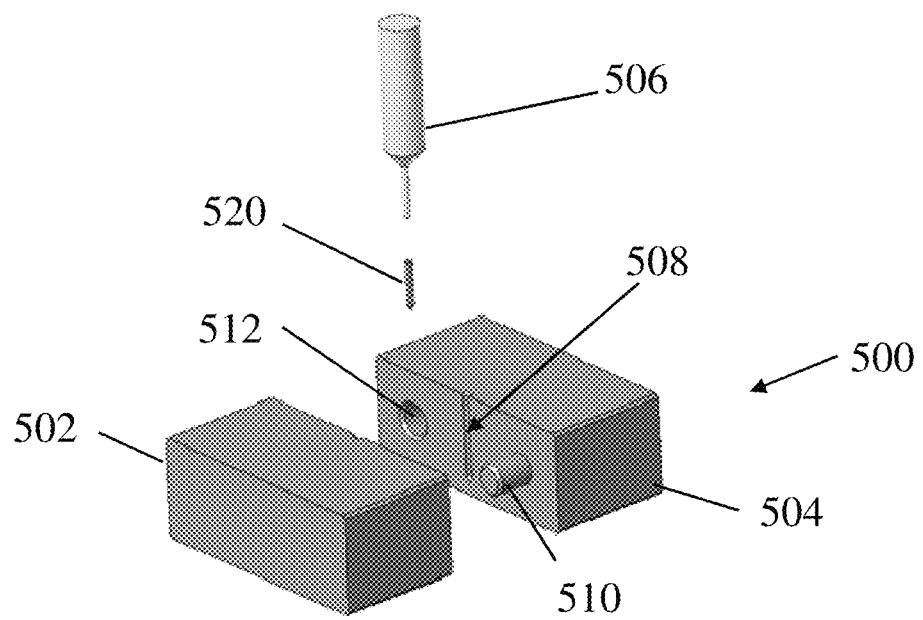
FIG. 6B is an exploded view of the mold of FIG. 6A.

Referring now to FIGS. 6A-6B, another embodiment of a mold 500 for forming a tissue interfacing component is described in more detail. Similar to the embodiments described above, the mold 500 includes first and second mold portions 502 and 504 that are coupleable to each other to define a mold cavity 508, and a mold punch 506 is insertable into the mold cavity to compress a granular therapeutic agent and form a tissue interfacing component 520. In this embodiment, each of the mold portions includes alignment features to aid in aligning the mold portions. In particular, each mold portion includes a protrusion 510 and a recess 512. When coupling the mold portions together, a protrusion 510 on one mold portion is received in a corresponding recess 512 on the other mold portion. While the alignment features in this embodiment are depicted as cylindrical protrusions and corresponding round recesses, it should be understood that the current disclosure is not limited to any particular geometry or arrangement for the alignment features.

Figure 7:
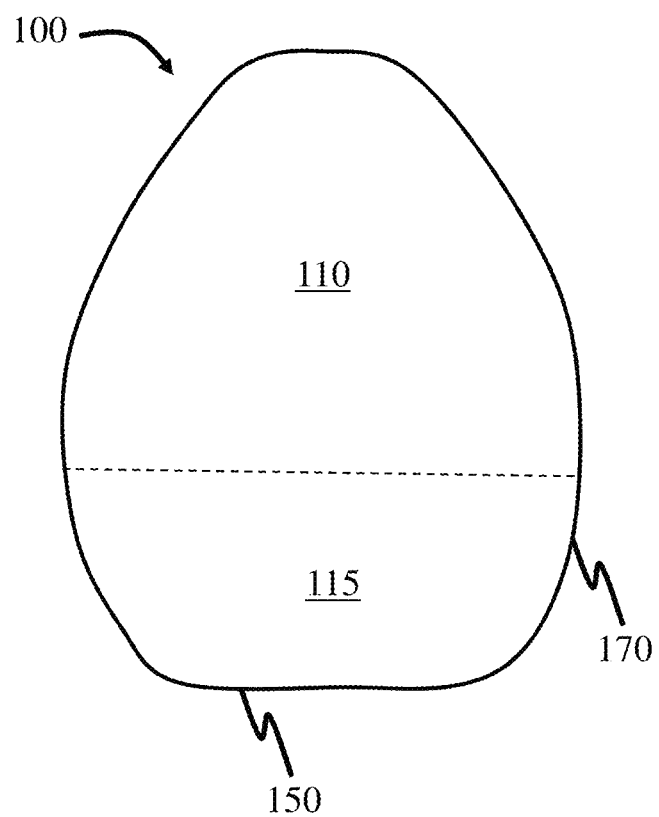
FIG. 7 is a schematic representation of an article for administering a tissue interfacing component, according to some embodiments.
Figure 8:
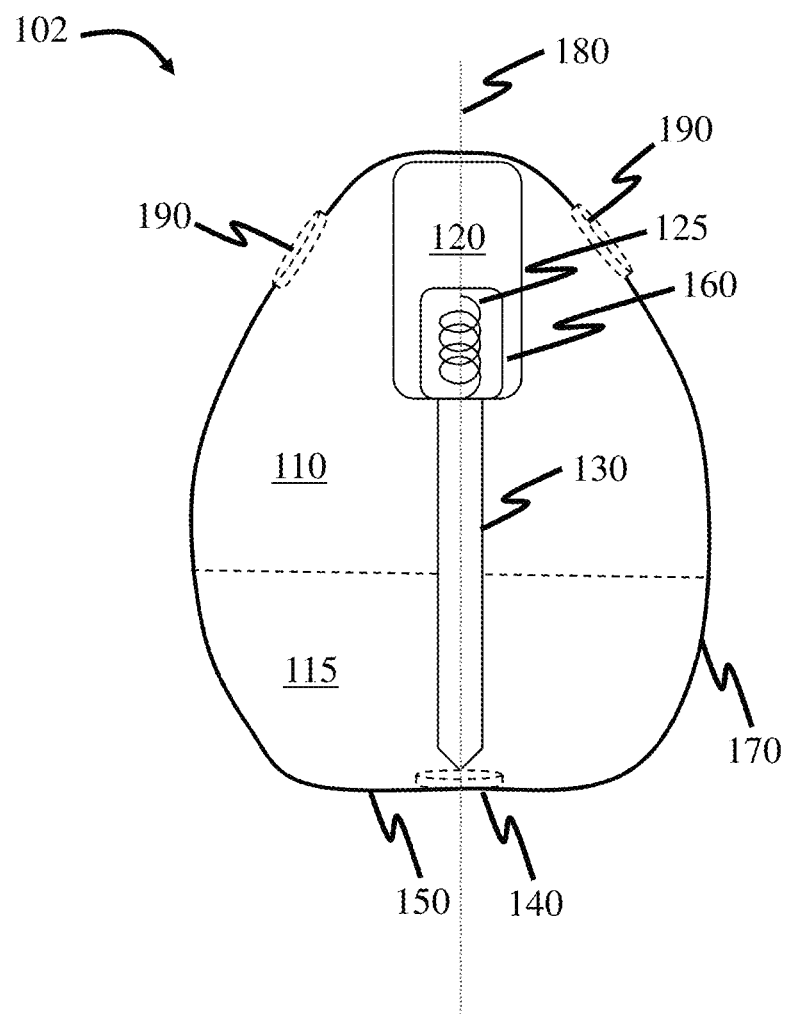
FIG. 8 is a schematic cross-sectional view of an article for administering a tissue interfacing component, according to some embodiments.
Figure 9:
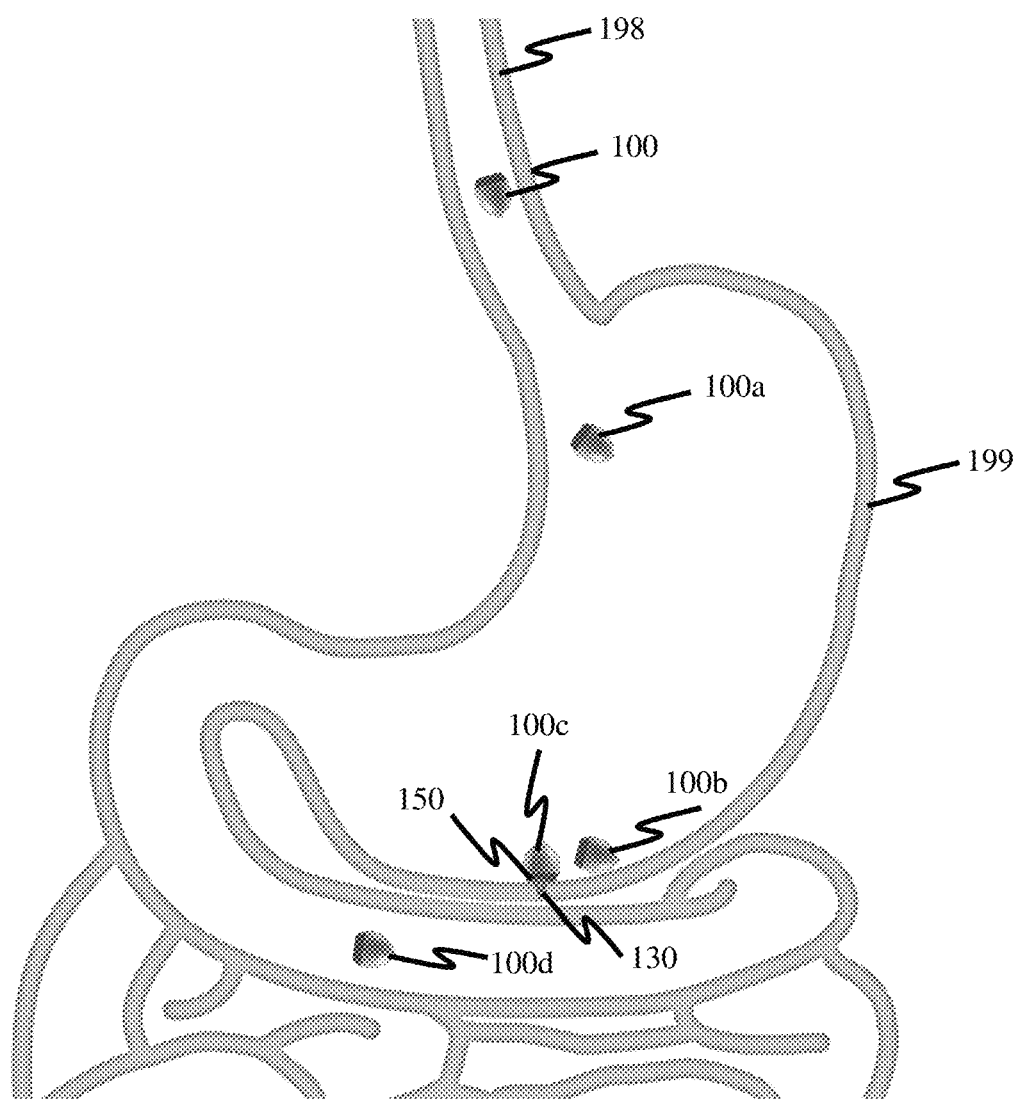
FIG. 9 is a schematic illustration of administration of an article for administering a tissue interfacing component, according to some embodiments.

Referring now to FIGS. 7-9, exemplary embodiments of an article for administering a tissue interfacing component such as a solid needle formed from a granular therapeutic agent are described in more detail. However, it should be understood that the presently disclosed tissue interfacing components may be deployed using any appropriate deployment device and are not limited to only being used with the device disclosed in the embodiment of FIGS. 7-9. In some embodiments, such articles may include a self-righting article, which may comprise a tissue interfacing component and a self-actuating component (e.g., comprising a spring and/or a support material) associated with the tissue interfacing component. As illustrated in FIG. 7, in some embodiments, a system 100 (e.g., a self-righting article) comprises a tissue-engaging surface 150. While embodiments described herein refer to a single tissue interfacing surface, in some embodiments, two or more tissue interfacing surfaces may be present. In certain embodiments, the self-righting article may be designed and configured such that the tissue-engaging surface contacts a surface (e.g., a surface of a tissue at a location internal to a subject such as a surface of a stomach of the subject). In some embodiments, system 100 will self-right (e.g., will orient without the need or use of external forces applied to the self-righting article) such that tissue-engaging surface 150 contacts the surface. In certain embodiments, the self-righting article is configured such that an axis essentially perpendicular to the tissue-engaging surface preferentially aligns parallel to the direction of gravity. The self-righting article may be configured such that the axis essentially perpendicular to the tissue-engaging surface is able to maintain an orientation of 20 degrees or less from vertical under externally applied torque. In some embodiments, the self-righting article is configured such that the tissue interfacing component has a longest longitudinal axis oriented within 15 degrees of vertical upon self-righting.

Without wishing to be bound by theory, the self-righting article may be designed to self-right as a result of a distribution of densities (and/or masses) within the self-righting article. For example, in some embodiments, system 100 (e.g., a self-righting article) comprises a first portion 110 and a second portion 115, the first portion and the second portion having different densities and/or different masses. In certain embodiments, the self-righting article may have a particular shape which enables the self-righting behavior. For example, as illustrated in FIG. 7, system 100 comprises a monostatic shape (e.g., a mono-monostatic shape, a gomboc-type shape) as indicated by external surface 170 of system 100. The term "monostatic" as used herein is given its ordinary meaning in the art and generally refers to a three-dimensional shape which has a single stable resting position (e.g., a point of balance). The term "mono-monostatic" as used herein is given its ordinary meaning in the art and generally refers to a three-dimensional shape having a single stable resting position and a single unstable resting positon. By way of example, and without wishing to be bound by theory, a sphere with a center of mass shifted from the geometrical center is general considered a mono-monostatic shape. The term "gomboc" as used herein is given its ordinary meaning in the art and generally refers to a convex three-dimensional shape which, when placed on a flat surface, has a single stable point of equilibrium (or orientation) and a single unstable point of equilibrium (or orientation). For example, and without wishing to be bound by theory, a gomboc-type shape when placed on a surface at any orientation other than the single stable orientation of the shape, then the shape will tend to re-orient to its single stable orientation.

FIG. 8 shows a cross-sectional illustration of an exemplary system 102. In some embodiments, system 102 comprises a self-actuating component 120. Self-actuating component 120 may be configured, e.g., upon exposure to a particular fluid, to release tissue interfacing component 130 associated with self-actuating component 120, from system 102. For example, in some cases, self-actuating component 120 comprises a spring 125 such that, upon actuation of the self-actuating component, spring 125 expands pushing tissue interfacing component 130 out of system 102 through hole 140 (associated with tissue engaging surface 150). In some cases, spring 125 comprises a support material 160 which maintains spring 125 under compression (e.g., under at least 5% compressive strain). In some cases, upon exposure of support material 160 and/or spring 125 to a fluid, the spring may be configured to release at least 10% (e.g., at least 20%, at least 30%, at least 40%, at least 50%, at least 60%, at least 70%, at least 80%, at least 90%, including any percentage therein) of a stored compressive energy of the spring (e.g., such that tissue interfacing component 130 is released and deployed from the opening of the system). In some embodiments, the spring is associated with the support material (e.g., at least partially encapsulated by the support material, in direct contact with the support material).

In some embodiments, the hole (e.g., hole 140 of FIG. 8) may comprise a fluidic gate (e.g., a plug, a coating, a membrane, or other appropriate barrier). In some cases, the fluidic gate may prevent a fluid (e.g., a fluid external to the system) from entering the system at the hole until a desired time. In certain embodiments, the fluidic gate comprises a barrier material. Non-limiting examples of suitable barrier materials include foils of polycaprolactone, thermoplastic elastomers, cellulose, and silicone. The barrier material may comprise one or more hydrophobic materials. In certain embodiments the barrier material may comprise one or more hydrophilic materials (e.g., sugar, PEG). Possible fabrication methods for these coatings include spray coating, dip coating, wrapping, deposition or other manufacturing methods. Alternatively, a fluidic gate may be a separately formed membrane or film that is assembled with the other components of the system. Those of ordinary skill in the art would be capable of selecting suitable hydrophobic and hydrophilic materials as a barrier material based upon the teachings of this specification.

In certain embodiments, tissue interfacing component 130 comprises an active pharmaceutical agent. In some embodiments, the active pharmaceutical agent may be present in the tissue interfacing component at relatively high amounts (e.g., greater than or equal to 10 wt %, greater than or equal to 80 wt %, or greater than or equal to 90 wt % API versus the total weight of the tissue interfacing component). The self-righting articles described herein may, in some cases, be administered to a subject e.g., such that the pharmaceutical agent is delivered to the subject. For example, in some cases, the article may be administered to the subject and a pharmaceutical agent is released from the article at a location internal to the subject.

In some embodiments, the system is administered to a subject (e.g., orally). In certain embodiments, the system may be administered orally, rectally, vaginally, nasally, or uretherally. In certain embodiments, upon reaching a location internal to the subject (e.g., the gastrointestinal tract), at least a portion of a support material degrades such that a spring extends and/or a tissue interfacing component interfaces (e.g., contacts, penetrates) with a tissue located internal to the subject. In some embodiments, the location internally of the subject is the colon, the duodenum, the ileum, the jejunum, the stomach, or the esophagus. In some embodiments, an active pharmaceutical ingredient may be released during and/or after penetration of the tissue located internal to the subject.

By way of example, and without wishing to be limited by such an exemplary set of embodiments, the system may be administered to a subject orally where it, in some cases, travels to the stomach of the subject, sinks to the bottom of the subject's stomach, and the system self-rights such that a tissue-engaging surface of the system contacts the stomach tissue (e.g., the system is at least partly supported by the stomach tissue). For example, as illustrated schematically in FIG. 9, exemplary system 100 may be administered to a subject (e.g., orally) such that system 100 enters gastrointestinal system 198 of the subject. System 100 may travel through gastrointestinal system 198 until reaching stomach 199 of the subject (system 100a). In some embodiments, system 100 may sink to the bottom of stomach 199 (system 100b) such that it contacts a surface of stomach 199. In certain embodiments, system 100 self-rights (system 100c) such that tissue engaging surface 150 of system 100 contacts the surface of stomach 199 and system 100 self-actuates such that tissue interfacing component 130 interfaces with a tissue at a location internal to a subject (e.g., the surface of stomach 199). While FIG. 9 illustrates interfacing of the tissue interfacing component with surface of the stomach 199, those of ordinary skill in the art would understand, based upon the teachings of this specification, that the tissue interfacing component may contact one or more layers underlying the surface of the stomach (or other location internal to the subject) including e.g., mucosal, sub-mucosal, and/or muscular tissue layer(s).

In some cases, as described herein, self-righting of system 100 may be driven by gravitational forces (e.g., acting on a center of mass of system 100). After a desired period of time, in some embodiments, system 100 disengages (e.g., tissue interfacing component 130 dissolves and/or is released) and exits stomach 199 (system 100d). The description above is not meant to be limiting and those of ordinary skill in the art would understand that other interactions between the system and the gastrointestinal system of a subject are also possible, as described herein. Additional aspects of self-righting articles that may be used to administer a tissue interfacing component are described in International Patent Application Pub. No. WO 2018/213600, entitled "SELF-RIGHTING SYSTEMS AND RELATED COMPONENTS AND METHODS", the contents of which are incorporated herein by reference.

While several embodiments of the present disclosure have been described and illustrated herein, those of ordinary skill in the art will readily envision a variety of other means and/or structures for performing the functions and/or obtaining the results and/or one or more of the advantages described herein, and each of such variations and/or modifications is deemed to be within the scope of the present disclosure. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings of the present invention is/are used. Those skilled in the art will recognize, or be able to ascertain using no more than routine experimentation, many equivalents to the specific embodiments of the invention described herein. It is, therefore, to be understood that the foregoing embodiments are presented by way of example only and that, within the scope of the appended claims and equivalents thereto, the present disclosure may be practiced otherwise than as specifically described and claimed. The present disclosure is directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the scope of the present disclosure.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Other elements may optionally be present other than the elements specifically identified by the "and/or" clause, whether related or unrelated to those elements specifically identified unless clearly indicated to the contrary. Thus, as a non-limiting example, a reference to "A and/or B," when used in conjunction with open-ended language such as "comprising" can refer, in one embodiment, to A without B (optionally including elements other than B); in another embodiment, to B without A (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

In the claims, as well as in the specification above, all transitional phrases such as "comprising," "including," "carrying," "having," "containing," "involving," "holding," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

Any terms as used herein related to shape, orientation, alignment, and/or geometric relationship of or between, for example, one or more articles, structures, forces, fields, flows, directions/trajectories, and/or subcomponents thereof and/or combinations thereof and/or any other tangible or intangible elements not listed above amenable to characterization by such terms, unless otherwise defined or indicated, shall be understood to not require absolute conformance to a mathematical definition of such term, but, rather, shall be understood to indicate conformance to the mathematical definition of such term to the extent possible for the subject matter so characterized as would be understood by one skilled in the art most closely related to such subject matter. Examples of such terms related to shape, orientation, and/or geometric relationship include, but are not limited to terms descriptive of: shape—such as, round, square, gomboc, circular/circle, rectangular/rectangle, triangular/triangle, cylindrical/cylinder, elliptical/ellipse, (n)polygonal/(n)polygon, etc.; angular orientation—such as perpendicular, orthogonal, parallel, vertical, horizontal, collinear, etc.; contour and/or trajectory—such as, plane/planar, coplanar, hemispherical, semi-hemispherical, line/linear, hyperbolic, parabolic, flat, curved, straight, arcuate, sinusoidal, tangent/tangential, etc.; direction—such as, north, south, east, west, etc.; surface and/or bulk material properties and/or spatial/temporal resolution and/or distribution—such as, smooth, reflective, transparent, clear, opaque, rigid, impermeable, uniform(ly), inert, non-wettable, insoluble, steady, invariant, constant, homogeneous, etc.; as well as many others that would be apparent to those skilled in the relevant arts. As one example, a fabricated article that would described herein as being "square" would not require such article to have faces or sides that are perfectly planar or linear and that intersect at angles of exactly 90 degrees (indeed, such an article can only exist as a mathematical abstraction), but rather, the shape of such article should be interpreted as approximating a "square," as defined mathematically, to an extent typically achievable and achieved for the recited fabrication technique as would be understood by those skilled in the art or as specifically described. As another example, two or more fabricated articles that would described herein as being "aligned" would not require such articles to have faces or sides that are perfectly aligned (indeed, such an article can only exist as a mathematical abstraction), but rather, the arrangement of such articles should be interpreted as approximating "aligned," as defined mathematically, to an extent typically achievable and achieved for the recited fabrication technique as would be understood by those skilled in the art or as specifically described.

What is claimed is:

1. A method of forming a tissue interfacing component, the method comprising:
    depositing a first granular therapeutic agent into a mold cavity of a mold, the mold cavity defining an elongated shape extending along a longitudinal axis from an opening of the mold cavity to a distal tip at a distal end of the mold cavity within the mold, wherein the distal tip is sized and shaped to facilitate insertion into tissue;
    compressing the first granular therapeutic agent within the mold along the longitudinal axis towards the distal end;
    forming a tissue interfacing component from the first granular therapeutic agent, at least in part, due to compression of the first granular therapeutic agent within the mold; and
    removing the tissue interfacing component from the mold cavity.

2. The method of claim 1, wherein compressing the first granular therapeutic agent comprises:
    inserting a mold punch into the opening of the mold cavity; and
    moving the mold punch along the longitudinal axis towards the distal end of the mold cavity.

3. The method of claim 1, wherein the mold comprises a first mold portion and a second mold portion selectively coupleable to one another to form the mold cavity.

4. The method of claim 3, wherein the mold comprises at least three mold portions that are coupleable to one another to form the mold cavity.

5. The method of claim 3, wherein the first and second mold portions comprise corresponding wall portions that define the mold cavity when the first and second mold portions are coupled to one another.

6. The method of claim 5, wherein each of the wall portions extend from the opening of the mold cavity to the distal tip of the mold cavity when the first and second mold portions are coupled to one another.

7. The method of claim 5, wherein the mold cavity is a blind cavity.

8. The method of claim 3, wherein removing the tissue interfacing component from the mold cavity comprises separating the first and second mold portions.

9. The method of claim 8, wherein separating the first and second mold portions comprises separating the first and second mold portions along a separating plane parallel to the longitudinal axis of the mold cavity.

10. The method of claim 9, wherein the distal tip of the mold cavity is positioned on the separating plane when the first and second mold sections are coupled to one another.

11. The method of claim 1, wherein the distal tip of the mold cavity defines a pointed tip or sharp edge at the distal end of the mold cavity.

12. The method of claim 1, wherein the longitudinal axis is aligned with a vertical direction, and wherein depositing the first granular therapeutic agent into the mold cavity comprises depositing the first granular therapeutic agent along the vertical direction.

13. The method of claim 1, further comprising depositing a second granular material into the mold cavity after depositing the first granular therapeutic agent into the mold cavity.

14. The method of claim 13, wherein compressing the first granular therapeutic agent within the mold comprises compressing the first granular therapeutic agent and the second granular material together within the mold.

15. The method of claim 13, wherein the tissue interfacing component comprises a distal portion formed from the first granular therapeutic agent and a proximal portion formed from the second granular material.

16. The method of claim 1, wherein removing the tissue interfacing component from the mold comprises ejecting the tissue interfacing component from the mold.

17. A method of forming a tissue interfacing component, comprising:
    depositing a first granular therapeutic agent into a mold cavity of a mold;
    applying a pressure to at least a portion of the first granular therapeutic agent of greater than or equal to 20 MPa to compress the first granular therapeutic agent and form the tissue interfacing component; and
    separating a first portion and a second portion of the mold along a plane parallel to a longitudinal axis of the mold cavity;
    wherein the therapeutic agent comprises greater than or equal to 80 wt % of the total tissue interfacing component weight, and
    wherein the tissue interfacing component is configured to penetrate at least 1 mm into human gastrointestinal mucosal tissue with a force of less than or equal to 5 N.

18. The method of claim 17, wherein applying the pressure to the first granular therapeutic agent comprises:
    inserting a mold punch into an opening of the mold cavity of the mold; and
    moving the mold punch along the longitudinal axis of the mold cavity towards a distal end of the mold cavity.

19. The method of claim 17, wherein the tissue interfacing component comprises a distal tip sized and shaped to facilitate insertion into tissue.

20. The method of claim 17, wherein the tissue interfacing component has an average cross-sectional dimension of greater than or equal to 0.5 mm.

21. The method of claim 17, wherein the tissue interfacing component is a needle.

22. The method of claim 17, further comprising depositing a second granular material into the mold after depositing the first granular therapeutic agent into the mold.

23. The method of claim 22, wherein applying the pressure to the first granular therapeutic agent within the mold comprises applying the pressure to the first granular therapeutic agent and the second granular material together within the mold.

24. The method of claim 17, wherein the first granular therapeutic agent is mixed with a binder comprising less than or equal to 20 wt % of the total tissue interfacing component weight.

* * * * *